US012630665B2

(12) United States Patent
Shin et al.

(10) Patent No.: US 12,630,665 B2
(45) Date of Patent: May 19, 2026

(54) FUNCTIONALIZED THERMOPLASTIC POLYURETHANE, METHOD FOR PRODUCING SAME, METHOD FOR PRODUCING HIGHLY FUNCTIONAL MEDICAL COMPOSITE MATERIAL USING SAME, AND MEDICAL DEVICE INCLUDING SAME

(71) Applicant: I-sens, Inc., Seoul (KR)

(72) Inventors: Hyunseo Shin, Seoul (KR); Bona Yang, Seoul (KR); Young Jea Kang, Seoul (KR); Geunhee Kang, Seoul (KR)

(73) Assignee: I-SENS, INC., Seoul (KR)

( * ) Notice: Subject to any disclaimer, the term of this patent is extended or adjusted under 35 U.S.C. 154(b) by 602 days.

(21) Appl. No.: 18/014,199

(22) PCT Filed: Jul. 8, 2021

(86) PCT No.: PCT/KR2021/008738
§ 371 (c)(1),
(2) Date: Jan. 3, 2023

(87) PCT Pub. No.: WO2022/010288
PCT Pub. Date: Jan. 13, 2022

(65) Prior Publication Data

US 2023/0257507 A1 Aug. 17, 2023

(30) Foreign Application Priority Data

Jul. 8, 2020 (KR) ........................ 10-2020-0084324

(51) Int. Cl.
*C08G 18/67* (2006.01)
*C07C 43/178* (2006.01)
(Continued)

(52) U.S. Cl.
CPC .......... *C08G 18/675* (2013.01); *C07C 43/178* (2013.01); *C07C 217/08* (2013.01);
(Continued)

(58) Field of Classification Search
None
See application file for complete search history.

(56) References Cited

U.S. PATENT DOCUMENTS 3,823,201 A 7/1974 Pizzini et al.
3,935,277 A 1/1976 Dear et al.
(Continued)

FOREIGN PATENT DOCUMENTS

CN 101255230 9/2008
CN 102086249 6/2011
(Continued)

OTHER PUBLICATIONS

Thorsten Anders et al., "Synthesis of a Difunctional Orthogonal Coupler for the Preparation of Carbohydrate- Functionalized sP(EO-stat-PO) Hydrogels", Macromol. Biosci. 2011, 11, 1201-1210, Jun. 16, 2011.
(Continued)

*Primary Examiner* — Eli D. Strah
(74) *Attorney, Agent, or Firm* — LEX IP MEISTER, PLLC

(57) ABSTRACT

The present invention pertains to: a functionalized thermoplastic polyurethane containing a novel chain extender having functionality capable of chemically bonding to a prepolymer polymerized by reacting a polyol (P) with a diisocyanate (R); a functional composite material containing one or more monomers or polymers selected from the group consisting of an anionic functional group, an amphoteric
(Continued)

functional group, a perfluorinated compound, a hydrogel, and a silicone polymer; a method for producing same; and an article including same.

2 Claims, 4 Drawing Sheets

(51) Int. Cl.

| | |
|---|---|
| ***C07C 217/08*** | (2006.01) |
| ***C07C 323/12*** | (2006.01) |
| ***C08G 18/10*** | (2006.01) |
| ***C08G 18/24*** | (2006.01) |
| ***C08G 18/32*** | (2006.01) |
| ***C08G 18/42*** | (2006.01) |
| ***C08G 18/44*** | (2006.01) |
| ***C08G 18/48*** | (2006.01) |
| ***C08G 18/61*** | (2006.01) |
| ***C08G 18/75*** | (2006.01) |
| ***C08G 18/83*** | (2006.01) |
| ***C08G 18/87*** | (2006.01) |
| ***C08G 77/458*** | (2006.01) |
| ***C08G 81/02*** | (2006.01) |
| ***C08L 75/04*** | (2006.01) |
| ***C08L 75/14*** | (2006.01) |
| ***C08L 75/16*** | (2006.01) |
| *A61B 5/1468* | (2006.01) |

(52) U.S. Cl.

CPC ............ *C07C 323/12* (2013.01); *C08G 18/10* (2013.01); *C08G 18/246* (2013.01); *C08G 18/3206* (2013.01); *C08G 18/4266* (2013.01); *C08G 18/44* (2013.01); *C08G 18/4825* (2013.01); *C08G 18/4833* (2013.01); *C08G 18/61* (2013.01); *C08G 18/758* (2013.01); *C08G 18/833* (2013.01); *C08G 18/835* (2013.01); *C08G 18/836* (2013.01); *C08G 18/837* (2013.01); *C08G 18/87* (2013.01); *C08G 77/458* (2013.01); *C08G 81/024* (2013.01); *C08L 75/04* (2013.01); *C08L 75/14* (2013.01); *C08L 75/16* (2013.01); *A61B 5/1468* (2013.01); *C08G 18/83* (2013.01); *C08G 2210/00* (2013.01); *C08L 2203/02* (2013.01); *C08L 2203/20* (2013.01)

(56) References Cited

U.S. PATENT DOCUMENTS

| | | | |
|---|---|---|---|
| 5,430,121 | A | 7/1995 | Pudleiner et al. |
| 2001/0037009 | A1 | 11/2001 | Sadvary |
| 2010/0032090 | A1 | 2/2010 | Myung et al. |
| 2012/0004351 | A1 | 1/2012 | Huang et al. |
| 2017/0183441 | A1 | 6/2017 | Makal |
| 2018/0009932 | A1 | 1/2018 | Hearon et al. |
| 2018/0105665 | A1 | 4/2018 | Day et al. |
| 2019/0106525 | A1* | 4/2019 | Becker ................. C08G 18/834 |
| 2019/0276583 | A1* | 9/2019 | Joy .................... C08G 18/0823 |

FOREIGN PATENT DOCUMENTS

| | | |
|---|---|---|
| CN | 105754026 | 7/2016 |
| CN | 106752754 | 5/2017 |
| CN | 108129636 | 6/2018 |
| CN | 110144033 | 8/2019 |
| CN | 110734536 | 1/2020 |
| EP | 2522684 | 11/2012 |
| EP | 2522685 | 11/2012 |
| EP | 3508510 | 7/2019 |
| JP | S57-177013 | 10/1982 |
| JP | H05-238960 | 9/1993 |
| JP | 2000-128950 | 5/2000 |
| JP | 2001-062389 | 3/2001 |
| JP | 2001-514401 | 9/2001 |
| JP | 2008-179812 | 8/2008 |
| JP | 2009-132773 | 6/2009 |
| JP | 2010-007058 | 1/2010 |
| JP | 2013-518147 | 5/2013 |
| JP | 2018-506626 | 3/2018 |
| JP | 2019-504922 | 2/2019 |
| JP | 2020-50832 | 4/2020 |
| KR | 10-2011-0040969 | 4/2011 |
| KR | 10-2016-0107443 | 9/2016 |
| KR | 10-2017-0140329 | 12/2017 |
| WO | 2016/126703 | 8/2016 |

OTHER PUBLICATIONS

Wang Guojian, "The modern Methods and Technology of Polymer Synthesis", Tongji University Press, Jul. 2013.
SIPO, Office Action of CN 202180051169.8 dated Aug. 28, 2024.
KIPO, PCT Search Report & Written Opinion of PCT/KR2021/008738 dated Oct. 13, 2021.
IP Australia, Office Action of the corresponding AU Patent Application No. 2021304167 dated Dec. 7, 2023.
EPO, the supplementary European Search Report of the corresponding EP Patent Application No. 21838208.3 dated Nov. 28, 2023.

* cited by examiner

[FIG. 1]
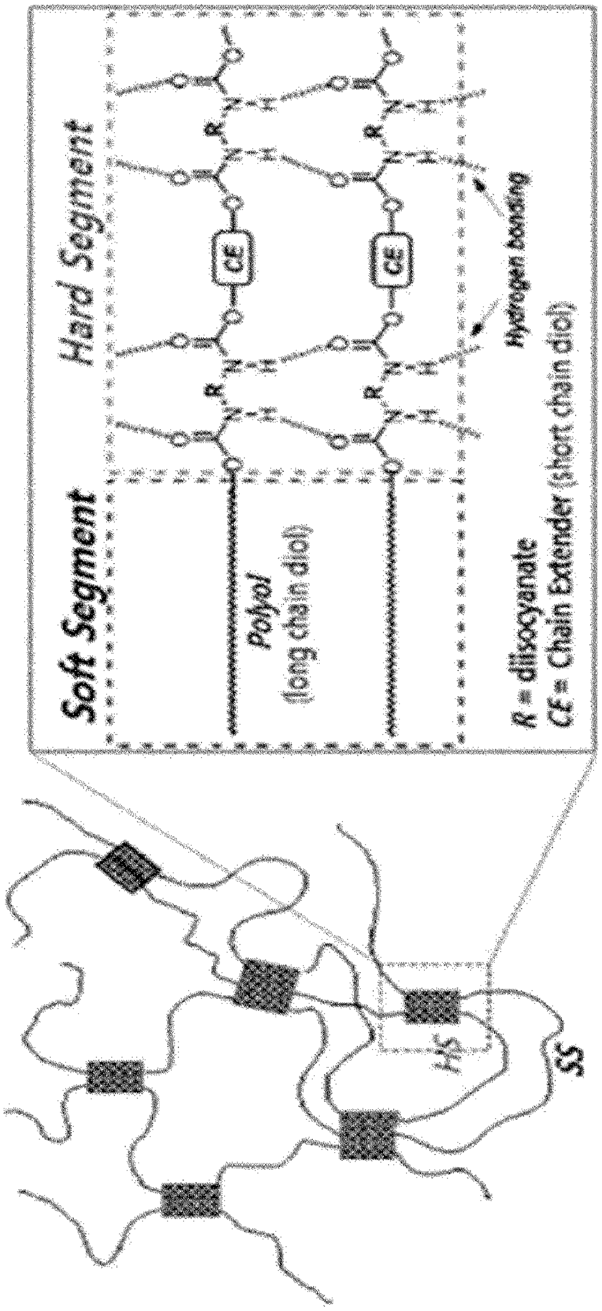

【FIG. 2】
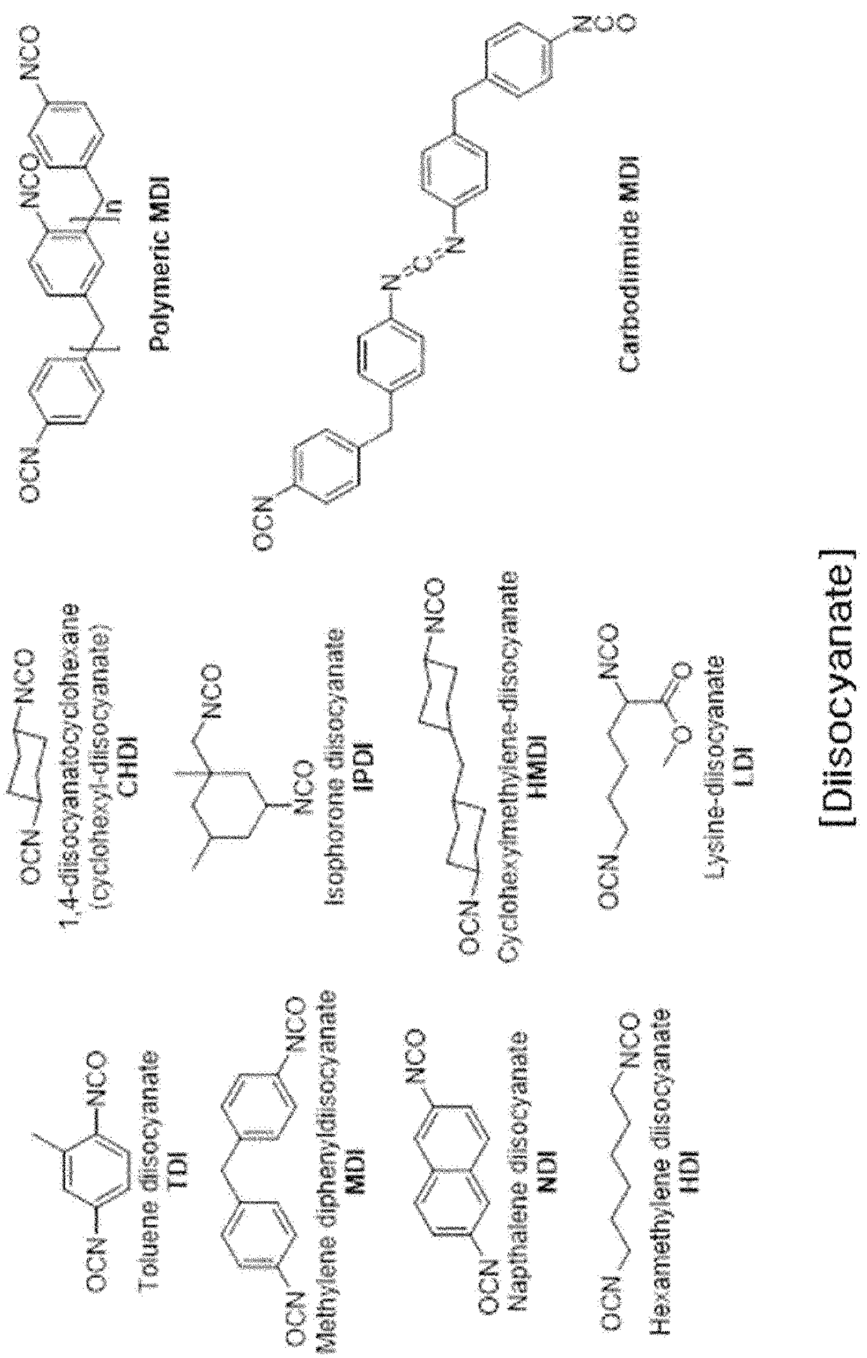
Toluene diisocyanate
TDI
1,4-diisocyanatocyclohexane
(cyclohexyl-diisocyanate)
CHDI
Polymeric MDI
Methylene diphenyldiisocyanate
MDI
Isophorone diisocyanate
IPDI
Napthalene diisocyanate
NDI
Cyclohexylmethylene-diisocyanate
HMDI
Carbodiimide MDI
Hexamethylene diisocyanate
HDI
Lysine-diisocyanate
LDI
[Diisocyanate]

[FIG. 3]

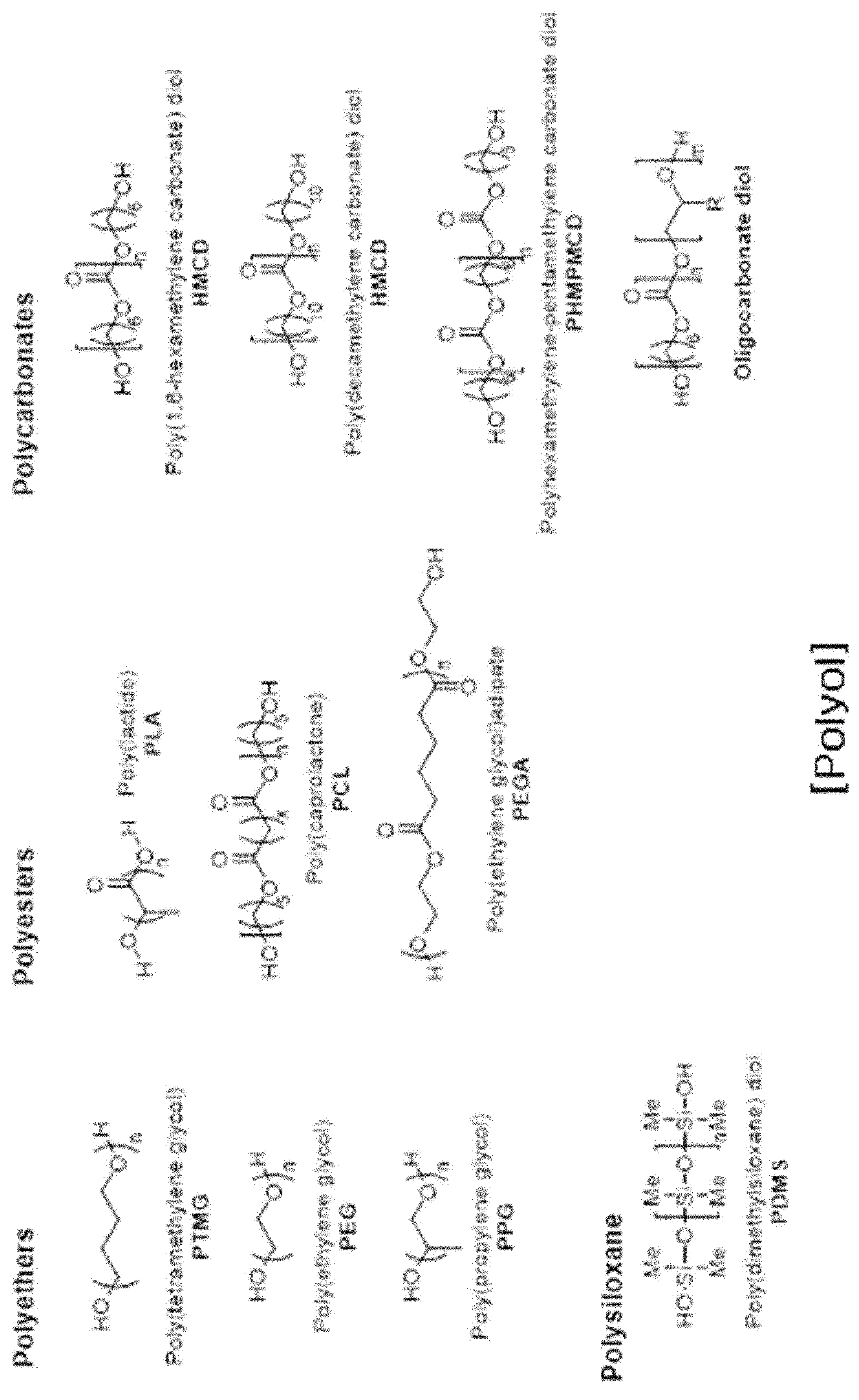

Polyethers

Poly(tetramethylene glycol)
PTMG

Poly(ethylene glycol)
PEG

Poly(propylene glycol)
PPG

Polysiloxane

Poly(dimethylsiloxane) diol
PDMS

Polyesters

Poly(lactide)
PLA

Poly(caprolactone)
PCL

Poly(ethylene glycol)adipate
PEGA

Polycarbonates

Poly(1,6-hexamethylene carbonate) diol
HMCD

Poly(decamethylene carbonate) diol
HMCD

Polyhexamethylene-pentamethylene carbonate diol
PHMPMCD

Oligocarbonate diol

[Polyol]

【FIG. 4】
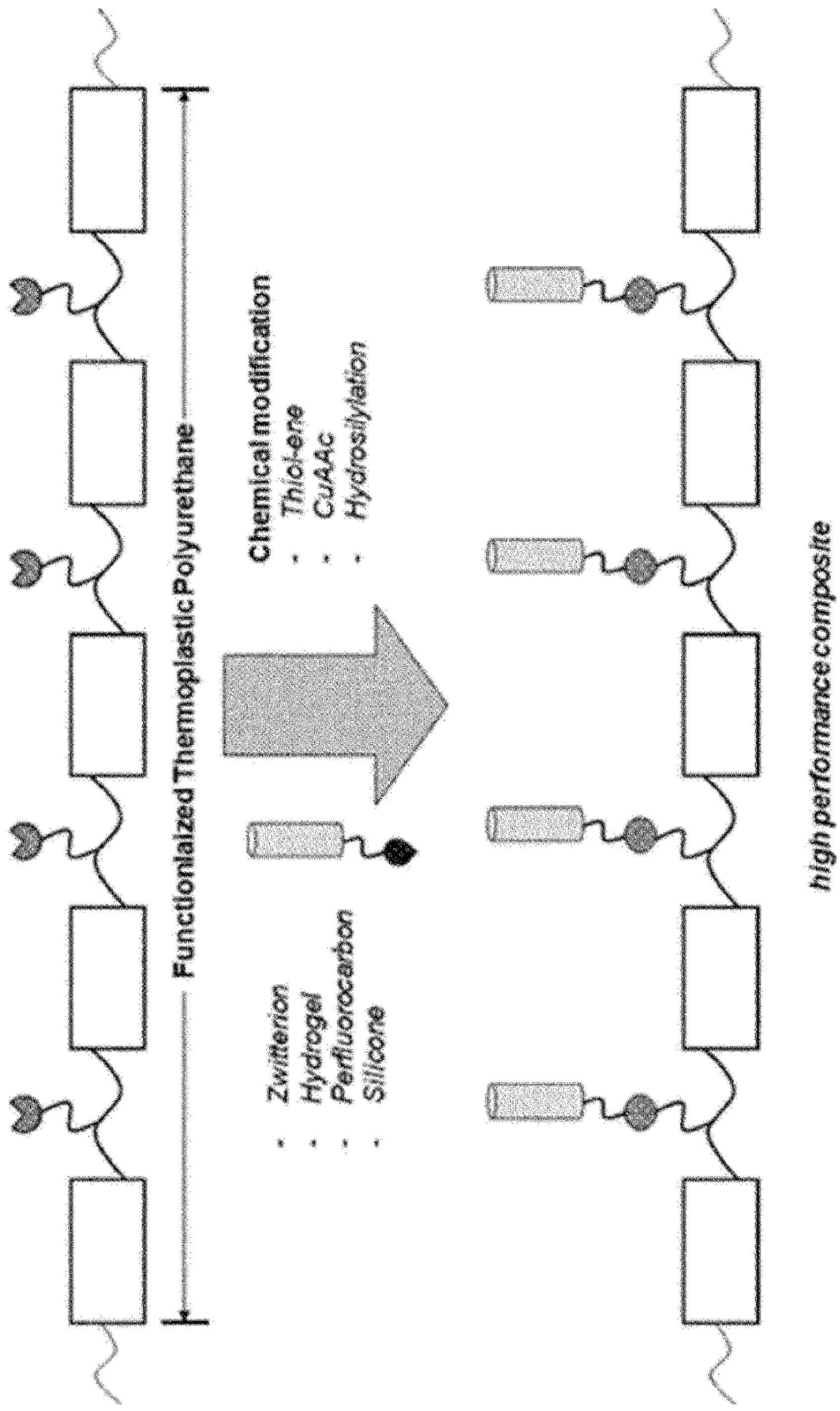

FUNCTIONALIZED THERMOPLASTIC POLYURETHANE, METHOD FOR PRODUCING SAME, METHOD FOR PRODUCING HIGHLY FUNCTIONAL MEDICAL COMPOSITE MATERIAL USING SAME, AND MEDICAL DEVICE INCLUDING SAME

TECHNICAL FIELD

The present invention relates to a novel chain extender having functionality capable of chemical bonding for each repeating unit of thermoplastic polyurethane, and novel functional thermoplastic polyurethane (hereinafter, also referred to as "TPU"), and more specifically, a method for producing and combining TPUs having various chemical properties using a novel chain extender with a said functionality, which can easily introduce new functionality through click reaction, thiol-ene reaction, hydrosilylation, and the like, while having mechanical properties similar to those of conventional thermoplastic polyurethane.

BACKGROUND ART

Thermoplastic polyurethane (TPU) is a kind of polyurethane plastics with several properties, including elasticity; transparency; resistance to oil, grease and abrasion. Technically, they are thermoplastic elastomers composed of linear segment block copolymers composed of hard segments and soft segments (See FIGS. 1 and 2).

Such TPU is widely used throughout the industry as a biocompatible material according to the characteristics of very excellent mechanical properties and chemical structure. Recently, studies are underway to introduce additional chemical properties to the above characteristics and use them in various customized special materials. However, since the conventional TPU does not have a reactive group in the polymer after it is prepared according to each use, it is almost impossible to prepare a monomer or a polymer in the form of a chemical bond expressing properties required by a user later. Therefore, the conventional TPU is used with additional properties in the form of coating or dispersion according to the user's requirement, and thus there are many restrictions on its use. In addition, the properties given to TPU by physical bonding as described above are not permanent and often limited to one-time use, due to phenomena such as abrasion, surface damage and detachment, and the like, depending on time and usage environment.

In order to solve the conventional problems with such TPU, the present inventors have manufactured a pre-TPU (functionalized thermoplastic polyurethane) with similar mechanical characteristics of general-purpose TPU, using a novel chain extender in which a functional group (e.g.; allyl, propargyl, thiol group, etc.) is linked in the preparation method of the conventional TPU, which is to combine polyol, diisocyanate and a chain extender, and have confirmed that various functionalities can be easily introduced through chemical reactions such as click reaction, thiol-ene reaction, hydrogen silylation reaction, and the like, thereby completing the present invention. According to the present invention, the TPU prepared according to the introduced functional group has various chemical properties, so it is possible to develop a polymer that can be used according to the specific use.

Disclosure

Technical Problem

In order to solve the problems of the prior art as described above, an object of the present invention is to provide a functionalized thermoplastic polyurethane copolymer comprising a chain extender having a functional group at each repeating unit of a polyurethane.

In addition, another object of the present invention is to provide a method for preparing the functionalized thermoplastic polyurethane copolymer.

Furthermore, other object of the present invention is to provide a composite for medical use, comprising the functionalized thermoplastic polyurethane copolymer and a method of preparing the same.

Moreover, other object of the present invention is to provide a medical device containing the thermoplastic polyurethane.

Technical Solution

In order to achieve the above objects, the present invention provides a functionalized thermoplastic polyurethane copolymer, represented by the structure as Chemical formula 1 below. Preferably, the functionalized thermoplastic polyurethane copolymer comprises a chain extender represented by Chemical formula 2.

[Chemical formula 1]

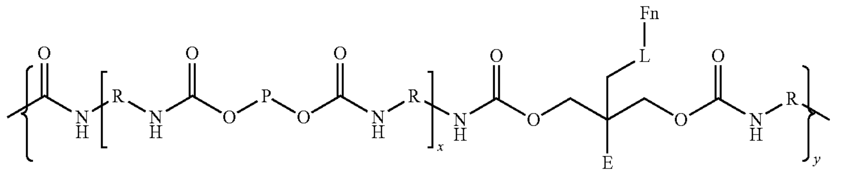

[Chemical formula 2]

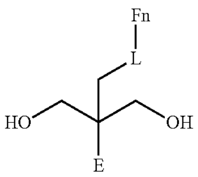

In the formula,

Fn is selected from the group consisting of a substituted or unsubstituted alkenyl group having 2 to 10 carbon atoms, a substituted or unsubstituted alkynyl group having 2 to 10 carbon atoms, a substituted or unsubstituted thiol group having 2 to 10 carbon atoms, a substituted or unsubstituted alkylazide group having 2 to 10 carbon atoms, a substituted or unsubstituted arylazide group having 7 to 20 carbon atoms, a substituted or unsubstituted alkylsilyl group having 2 to 10 carbon atoms, a substituted or unsubstituted isocyanate group having 2 to 10 carbon atoms, a substituted or unsubstituted alkylamino group having 2 to 20 carbon atoms, a substituted or unsubstituted alcohol group having 2 to 10 carbon atoms, a substituted or unsubstituted alkoxy group having 2 to 10 carbon atoms, and a substituted or unsubstituted alkylhalogen group having 2 to 20 carbon atoms;

L is one kind selected from the group consisting of O, C, S, N, P, Si, a substituted or unsubstituted alkyl group having 1 to 10 carbon atoms, a substituted or unsubstituted ethylene oxide group having 2 to 20 carbon atoms, a substituted or unsubstituted alkoxy group having 1 to 20 carbon atoms, a substituted or unsubstituted cycloalkyl group having 3 to 20 carbon atoms, a substituted or unsubstituted aryl group having 7 to 20 carbon atoms, a substituted or unsubstituted heteroaryl group having 3 to 15 carbon atoms, and a substituted or unsubstituted siloxane group having 5 to 20 carbon atoms;

E is one kind selected from the group consisting of a substituted or unsubstituted alkyl group having 1 to 10 carbon atoms, a substituted or unsubstituted ethylene oxide group having 2 to 20 carbon atoms, a substituted or unsubstituted alkoxy group having 1 to 20 carbon atoms, a substituted or unsubstituted cycloalkyl group having 3 to 20 carbon atoms, a substituted or unsubstituted aryl group having 7 to 20 carbon atoms, a substituted or unsubstituted heteroaryl group having 3 to 15 carbon atoms, and a substituted or unsubstituted siloxane group having 5 to 20 carbon atoms;

P is a polyol;

R is a diisocyanate;

x is an integer of 2 to 50; and y is an integer of 2 to 100.

Advantageous Effects

The functionalized thermoplastic polyurethane copolymer according to the present invention is excellent in that it introduces various functional groups into a chain extender, thereby not only solving problems in processing and preparation of the thermoplastic polyurethane, but also efficiently producing and preparing products with equivalent performance.

BRIEF DESCRIPTION OF THE DRAWINGS

FIG. 1 is a schematic diagram showing the structure of a thermoplastic polyurethane.

FIG. 2 is a diagram showing specific examples of isocyanate, which is a hard segment used in preparation of a thermoplastic polyurethane.

FIG. 3 is a diagram showing specific examples of polyol, which is a soft segment used in preparation of a thermoplastic polyurethane.

FIG. 4 is a schematic diagram for preparation of a high-performance composite using a functionalized thermoplastic polyurethane copolymer.

BEST MODE

Hereinafter, the present invention will be described in detail.

Preferably, the molecular weight of each polyol (P) may be 400 g/mol 10,000 g/mol, but not limited thereto.

The functionalized polyurethane according to the present invention is a thermoplastic polyurethane copolymer as a block copolymer of a polyol (P) and a diisocyanate (R).

The polyol (P) is a high molecular weight material prepared with an initiator and a monomer constituent unit, and when it is combined to polyurethane, it corresponds to a "soft segment" of the polymer, and it is present commonly in a coiled form. In a preferable aspect, the polyol (P) may be one or more kinds of polyols selected from the group consisting of polyether, polycarbonate, polyester and silicone.

In a non-limitative example, the polyether polyol may be one or more kinds selected from the group consisting of polyethyleneglycol (PEG), polypropyleneglycol (PPG) and polytetramethyleneglycol (PTMG), and the polycarbonate polyol may be one or more kinds selected from the group consisting of poly(1,6-hexamethylene carbonate)diol (PHMCD), poly(decamethylene carbonate)diol (PDMCD), oligocarbonate diol and polyhexamethylene-pentamethylene carbonate diol (PHMPMCD), and the polyester polyol may be one or more kinds selected from the group consisting of polylactide (PLA), polycaprolactone (PCL) and polyethyleneglycol adipate (PEGA), and the silicone polyol may be one or more kinds selected from the group consisting of polydimethyl siloxane (PDMS), polyaryl siloxane and polyalkyl siloxane.

In the present invention, the diisocyanate and chain extender composes a hard segment, and the hard segment is combined to a soft segment by covalent bonding. In a preferable aspect, the diisocyanate (R) may be one or more kinds selected from the group consisting of 4,4'-dicyclohexylmethane diisocyanate(HMDI), isophorone diisocyanate (IPDI), 1,4-cyclohexylmethane diisocyanate(CHDI), 4,4'-diphenylmethanediisocyanate(MDI), 2,4- or 2,6-toluene diisocyanate(TDI), carbodiimide-modified MDI, polymeric MDI, and hexamethylene diisocyanate.

The chain extender comprised in the functionalized thermoplastic polyurethane copolymer of the present invention is characterized by having various functional groups (E and Fn) to give the functionalized thermoplastic polyurethane copolymer functionality. Among these functional groups, Fn may be selected from the group consisting of a substituted or unsubstituted alkenyl group having 2 to 10 carbon atoms, a substituted or unsubstituted alkynyl group having 2 to 10 carbon atoms, a substituted or unsubstituted thiol group having 2 to 10 carbon atoms, a substituted or unsubstituted alkylazide group having 2 to 10 carbon atoms, a substituted or unsubstituted arylazide group having 7 to 20 carbon atoms, a substituted or unsubstituted alkylsilyl group having 2 to 10 carbon atoms, a substituted or unsubstituted isocyanate group having 2 to 10 carbon atoms, a substituted or unsubstituted alkylamino group having 2 to 20 carbon atoms, a substituted or unsubstituted alcohol group having 2 to 10 carbon atoms, a substituted or unsubstituted alkoxy group having 2 to 10 carbon atoms, and a substituted or unsubstituted alkylhalogen group having 2 to 20 carbon atoms.

In addition, E may be one or more kinds selected from the group consisting of a substituted or unsubstituted alkyl group having 1 to 10 carbon atoms, a substituted or unsubstituted ethylene oxide group having 2 to 20 carbon atoms, a substituted or unsubstituted alkoxy group having 1 to 20 carbon atoms, a substituted or unsubstituted cycloalkyl group having 3 to 20 carbon atoms, a substituted or unsubstituted aryl group having 7 to 20 carbon atoms, a substituted or unsubstituted heteroaryl group having 3 to 15 carbon atoms, and a substituted or unsubstituted siloxane group having 5 to 20 carbon atoms; and preferably, the unsubstituted alkenyl group having 2-10 carbon atoms may be for example, a vinyl group, an allyl group, a butenyl group, a pentenyl group or a hexenyl group, but not limited thereto, and the substituted or unsubstituted alkynyl group having 2 to 10 carbon atoms may be for example, propargyl, but-1-ynyl (butynyl), pentynyl or hexynyl, but not limited thereto.

The unsubstituted alkynyl group having 1-10 carbon atoms may be for example, a methyl group, an ethyl group, a propyl group, an isopropyl group, a n-butyl group, a sec-butyl group, a t-butyl group, a pentyl group, a hexyl group, a cyclohexyl group, a heptyl group, an octyl group or a decane group, but not limited thereto, and the substituted or unsubstituted ethylene oxide group having 2 to 20 carbon atoms may be, for example, one or more kinds selected from the group consisting of an ethylene oxide group having 1-10 n in $(-OCH_2CH_2-)_n$, but not limited thereto, and the substituted or unsubstituted alkoxy group having 1 to 20 carbon atoms may be for example, namely, a methoxy group, an ethoxy group, a propoxy group, an isopropoxy group, a butoxy group, a tert-butoxy group, a pentanoxy group, a hexanoxy group, a heptanoxy group, an octanoxy group, a decanoxy group, an alkyl-decanoxy group (2-hexyl-1-decanoxy, 6-ethyl-3-decanoxy, etc.), a dodecanoxy group, an alkyl-dodecanoxy group, a undecanoxy group, an alkyl-undecanoxy group, an allyloxy group, a cycloalkyloxy group, or a cyclohexyloxy group, but not limited thereto, and the substituted or unsubstituted cycloalkyl group having 3 to 20 carbon atoms may be for example, cyclopropyl cyclobutyl, cyclopentyl, cyclohexyl or cycloheptyl, but not limited thereto.

The substituted or unsubstituted aryl group or aryloxy group having 7 to 20 carbon atoms may be for example, a phenyl group, a benzyl group, a tolyl group, a naphthalene group, a phenanthrenyl group, other alkylphenyl group, and a phenyloxy group, a benzyloxy group, a tolyloxy group, a naphthaleneoxy group, a phenanthreneoxy group or other alkoxyphenyl group, but not limited thereto, and the substituted or unsubstituted heteroaryl group or heteroaryloxy group having 3 to 15 carbon atoms may be for example, monocyclic heteroaryl such as furyl, thiopenyl, pyrrolyl, imidazolyl, pyrazolyl, thiazolyl, thiadiazolyl, isothiazolyl, isooxazolyl, oxazolyl, oxadiazolyl, triazinyl, tetrazinyl, triazolyl, tetrazolyl, furazanyl, pyridyl, pyrazinyl, pyrimidinyl and pyridazinyl, polycyclic heteroaryl such as benzofuranyl, benzothiopenyl, isobenzofuranyl, benzoimidazolyl, benzothiazolyl, benzoisothiazolyl, benzoisoxazolyl, benzooxazolyl, isoindolyl, indolyl, indazolyl, benzothiadiazolyl, quinolyl, isoquinolyl, cinnolinyl, quinazolynyl, quinoxalinyl, carbazolyl, phenanthridinyl, benzodioxolyl, and the like, or a quaternary salt thereof, or the like, but not limited thereto, and the substituted or unsubstituted siloxane group having 5 to 20 carbon atoms may be for example, a siloxane group having 2-10 n in $(-(Me)_2SiO-)_n$, but not limited thereto.

Unless otherwise specified herein, the term "substituted" means that one or more hydrogen atoms are substituted with 1 to 3 substituents selected from the group consisting of a halogen atom (for example, F, Cl, Br or I), a cyano group, a hydroxy group, a thiol group, a nitro group, an amino group, an imino group, an azido group, an amidino group, a hydrazine group, a hydrazono group, an oxo group, a carbonyl group, a carbamyl group, an ester group, an ether group, a carboxy group or a salt thereof, a sulfoxane group or a salt thereof, phosphate or a salt thereof, an alkyl group having 1 to 6 carbon atoms, a haloalkyl group having 1 to 6 carbon atoms, an alkenyl group having 2 to 6 carbon atoms, a haloalkenyl group having 2 to 6 atoms, an alkynyl group having 2 to 6 carbon atoms, a haloalkynyl group having 2 to 6 carbon atoms, an alkoxy group having 1 to 6 carbon atoms, a haloalkoxy group having 1 to 6 carbon atoms, an alkylthio group having 1 to 20 carbon atoms, a carbocycle group having 3 to 20 carbon atoms (for example, a cycloalkyl group having 3 to 9 carbon atoms, a halocycloalkyl group having 3 to 9 carbon atoms, a halocycloalkyl group having 3 to 9 carbon atoms, a cycloalkenyl group having 3 to 9 carbon atoms, a halocycloalkynyl group having 3 to 9 carbon atoms, a heterocycloalkyl group having 3 to 9 carbon atoms, a heterocycloalkyl group having 3 to 9 carbon atoms, a heterocycloalkenyl group having 2 to 9 carbon atoms, a heterocycloalkenyl group having 2 to 9 carbon atoms) and a C1-20 hetero cycle group (for example, an aryl group having 6 to 20 carbon atoms, an aryloxy group having 6 to 20 carbon atoms, an arylthiol group having 6 to 30 carbon atoms, a heteroaryl group having 2 to 20 carbon atoms, a heteroaryloxy group having 2 to 20 carbon atoms, a heteroarylthio group having 2 to 20 carbon atoms).

In a specific aspect, the functionalized thermoplastic polyurethane copolymer according to the present invention may have a weight average molecular weight of 1,000 to 3,500,000 g/mol. Preferably, it may be 5,000 to 100,000, 50,000 to 1,000,000, or 250,000 to 2,000,000 g/mol.

Specifically, the functionalized thermoplastic polyurethane copolymer according to the present invention may be represented by the structure selected from the group consisting of Chemical formulas 3 to 14 below.

[Chemical formula 3]
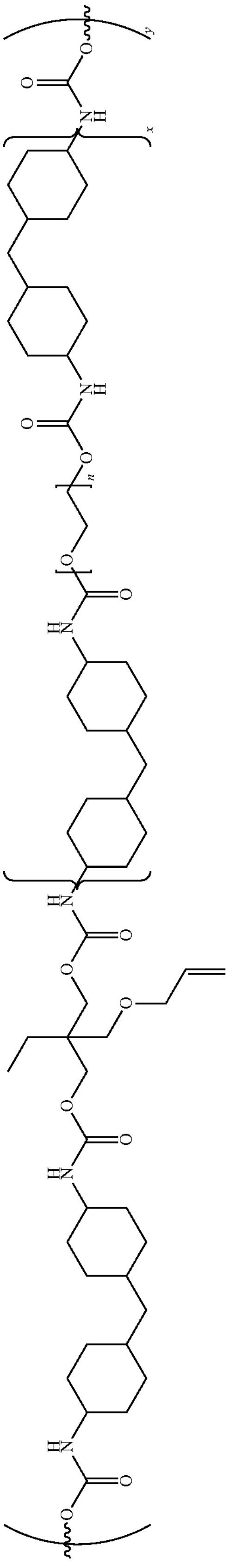
[Chemical formula 4]
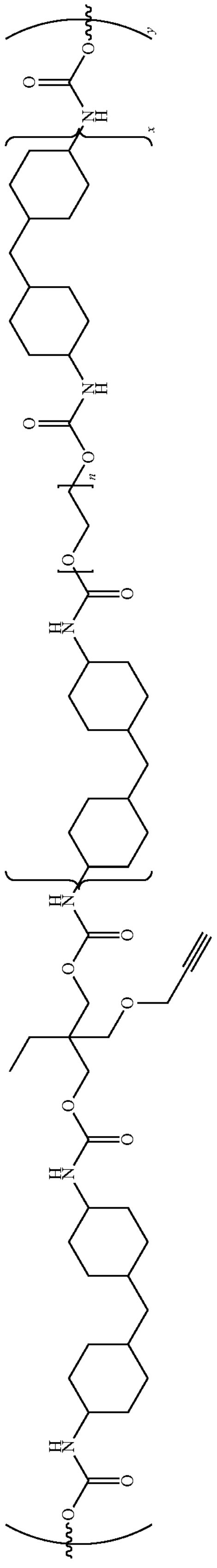
[Chemical formula 5]
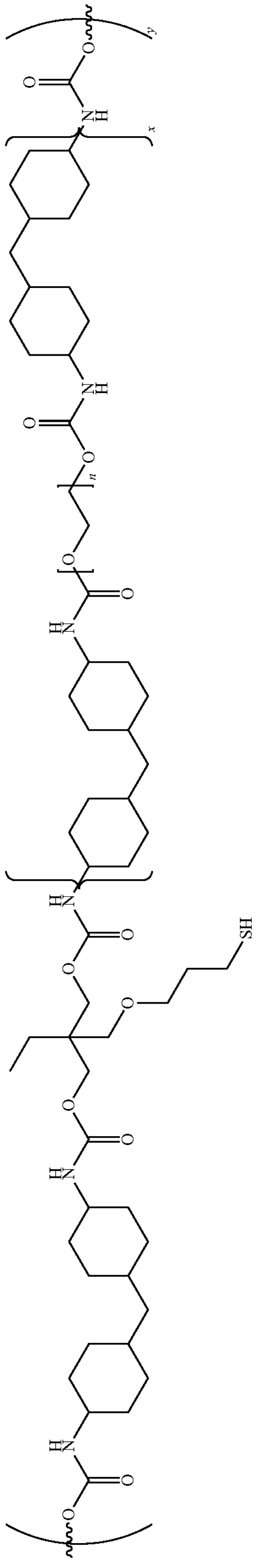

-continued
[Chemical formula 6]
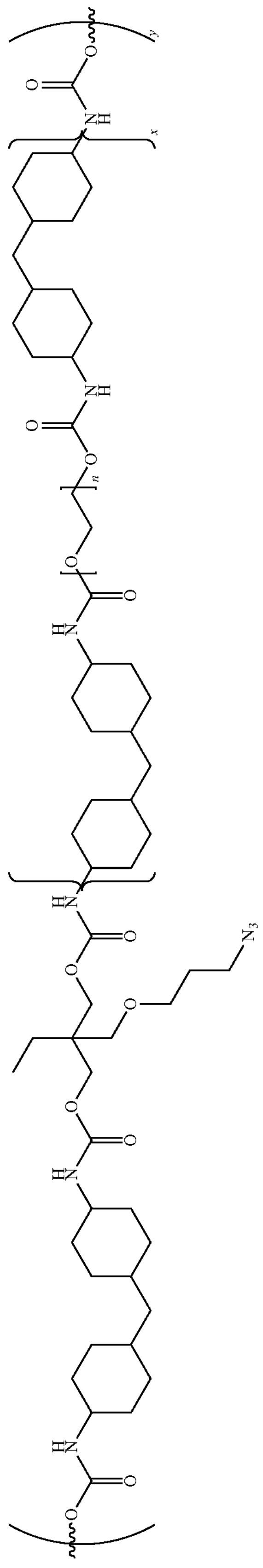
[Chemical formula 7]
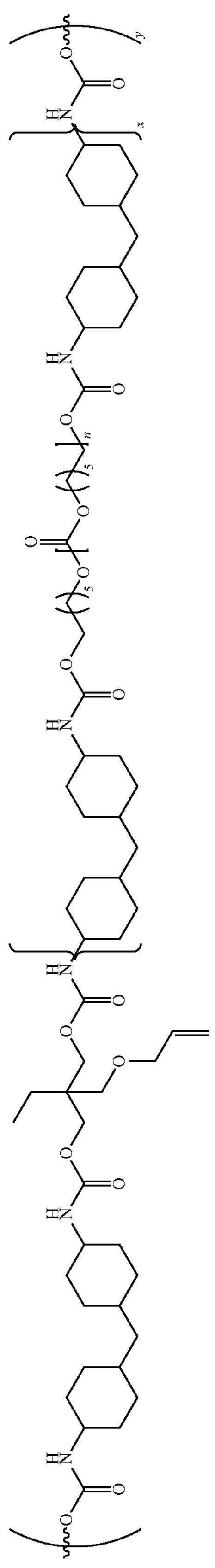
[Chemical formula 8]
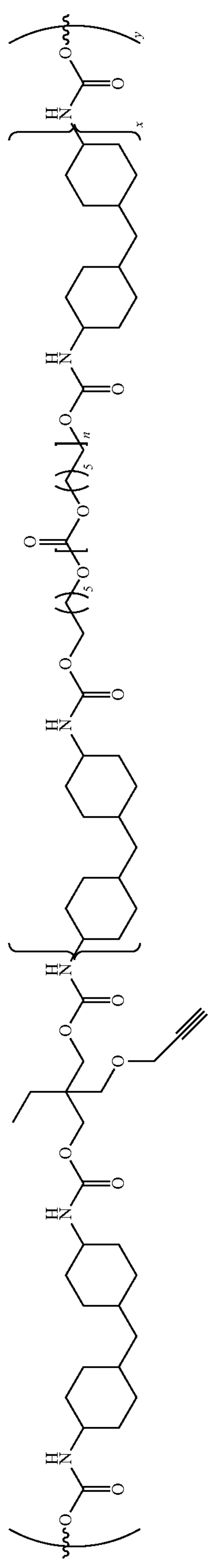
[Chemical formula 9]
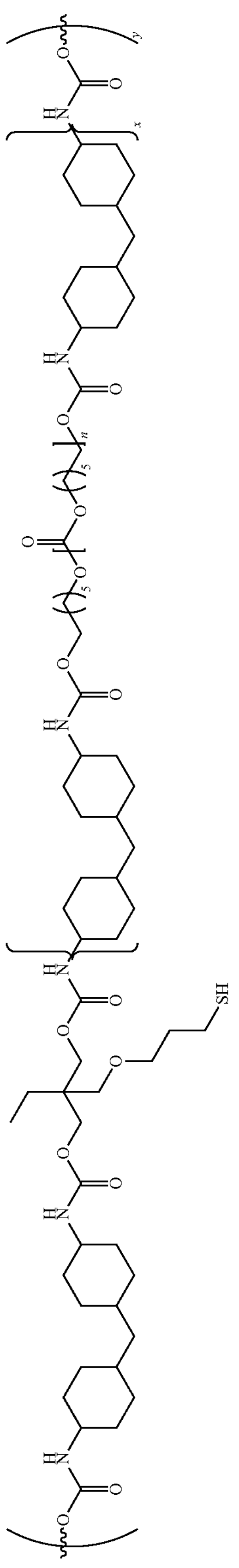

-continued
[Chemical formula 10]
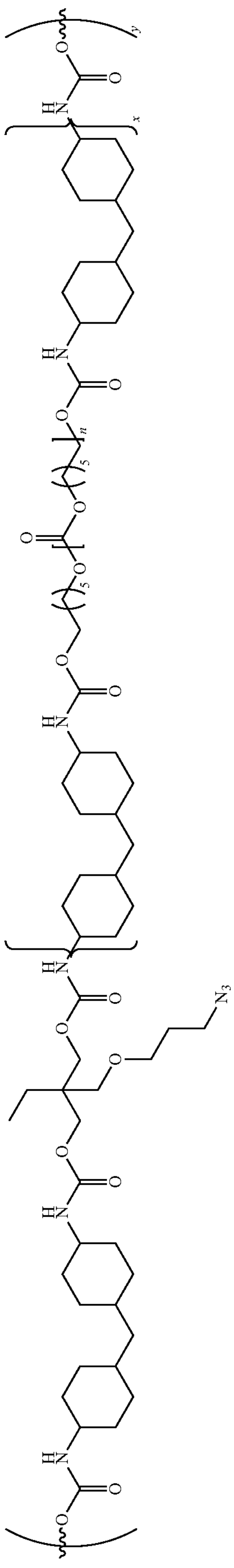
[Chemical formula 11]
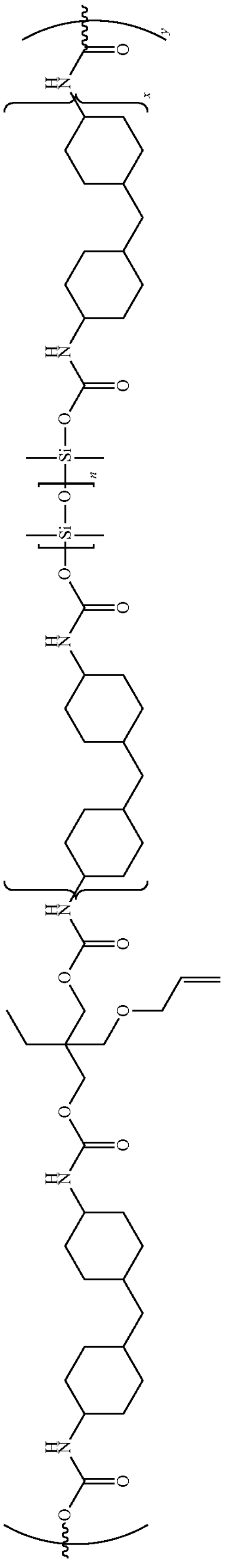
[Chemical formula 12]
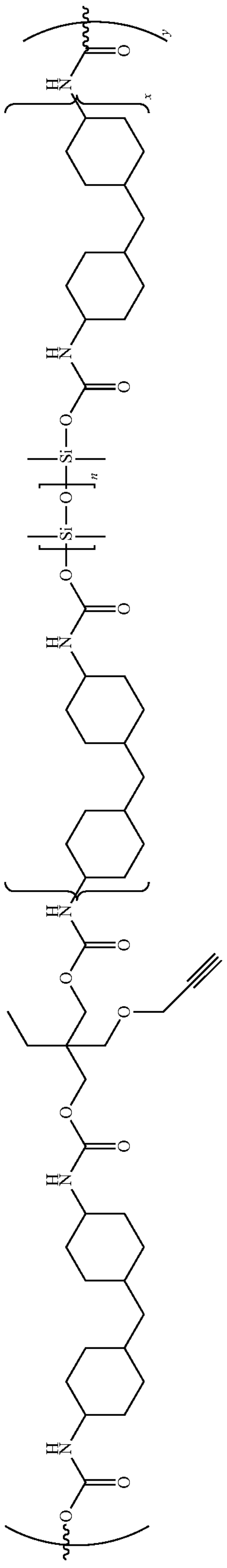

-continued
[Chemical formula 13]
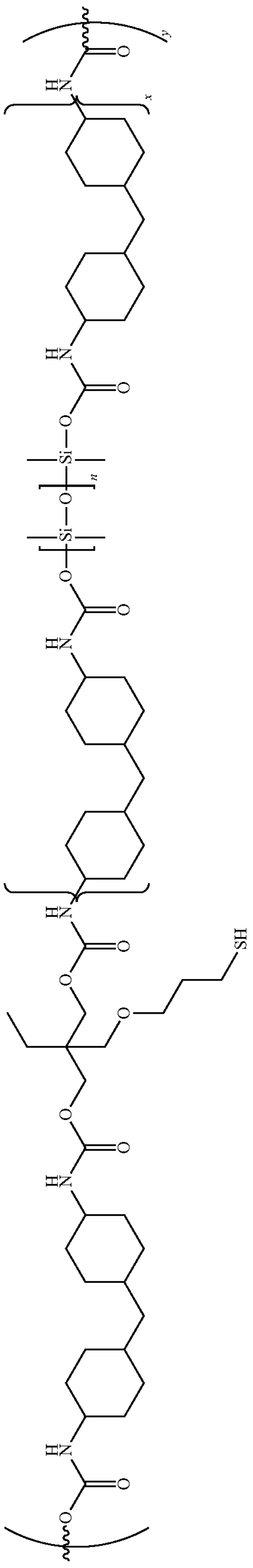
[Chemical formula 14]
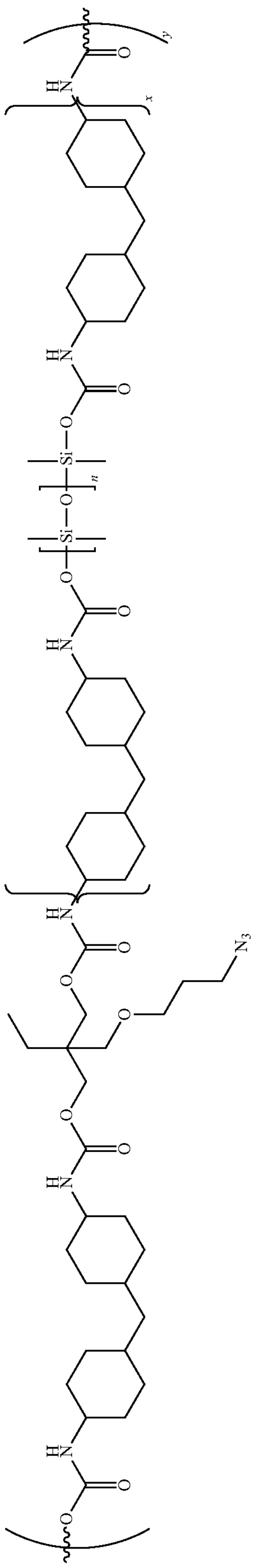

In the Chemical formulas 3 to 14, x and y are as defined in the Chemical formula 1, and n is an integer of 10 to 250.

In another aspect, the present invention relates to a chain extender represented by Chemical formula 2 below.

[Chemical formula 2]

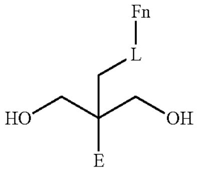

In the formula,

E, Fn and L are as defined in the Chemical formula 1, respectively.

Preferably, the chain extender of the Chemical formula 2 may be selected from the group consisting of Chemical formulas 15 to 18 below.

[Chemical formula 15]

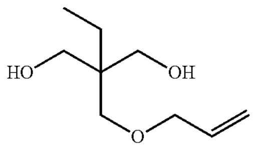

[Chemical formula 16]

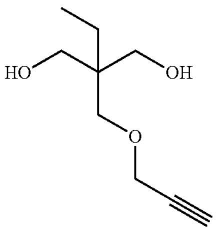

-continued

[Chemical formula 17]

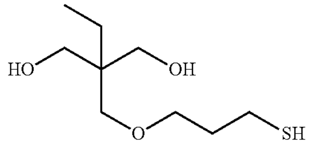

[Chemical formula 18]

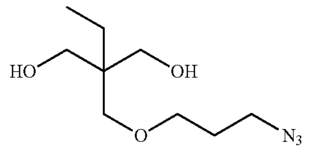

In an additional aspect, the present invention relates to a functional composite in which a monomer or polymer having various functional groups is introduced into a functionalized thermoplastic polyurethane copolymer. Preferably, the functional composite may be a medical composite. The example of the monomer or polymer having various functional groups may be one or two kinds selected from the group consisting of an anionic functional group, an amphoteric functional group, a perfluorinated compound, a hydrogel and a silicone polymer, but not limited thereto, and any monomer or polymer comprising a known functional group capable of giving desired functionality to the thermoplastic polyurethane may be used without limitation. The anionic functional group, amphoteric functional group, perfluorinated compound, hydrogel polymer and silicone polymer will be described in detail below.

As one specific example of the present invention, the functionalized medical composite in which an amphoteric functional group is introduced may be represented by the following Chemical formula 19.

[Chemical formula 19]

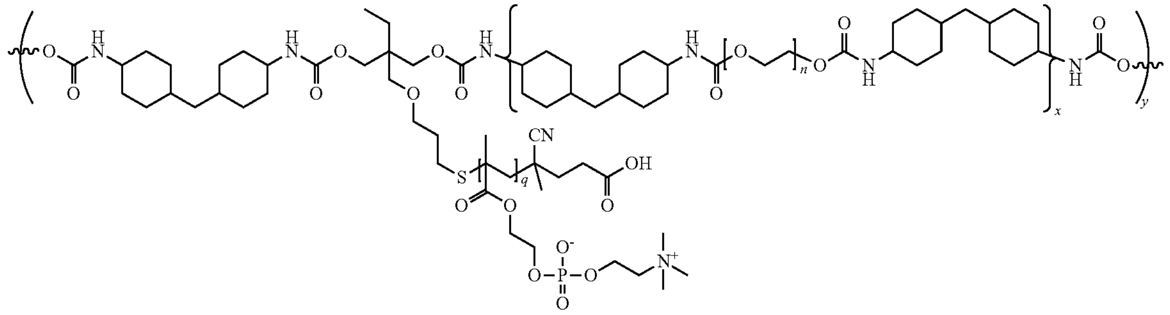

In the Chemical formula 19, x, y and n are as defined in the Chemical formulas 3 to 14, and q is an integer of 10 to 100.

As another example, the functionalized medical composite in which a hydrogel polymer is introduced may be represented by the following Chemical formula 20 or 21.

[Chemical formula 20]

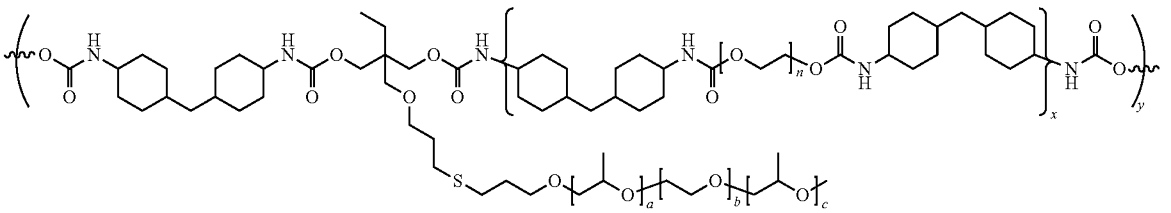

[Chemical formula 21]

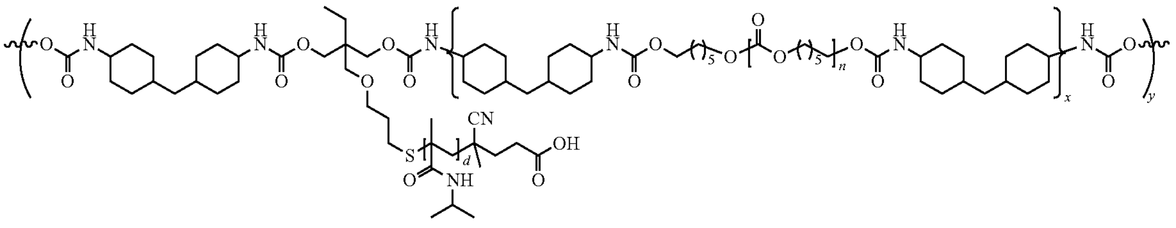

In the Chemical formulas 20 to 21, x, y and n are as defined in the Chemical formulas 3 to 14, and a, b, c and d are an integer of 10 to 100, respectively.

As one other example, the functionalized medical composite in which a perfluorinated compound is introduced may be represented by the following Chemical formula 22.

[Chemical formula 22]

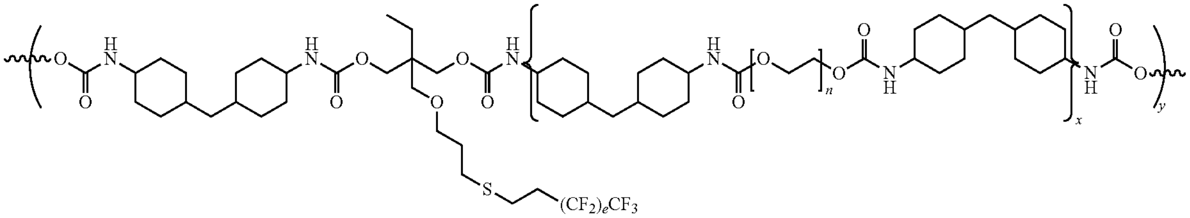

In the Chemical formula 22, x, y and n are as defined in the Chemical formulas 3 to 14, and e is an integer of 3 to 25, respectively.

As other one example, the functionalized medical composite in which a silicone polymer is introduced may be represented by the following Chemical formula 23.

[Chemical formula 23]

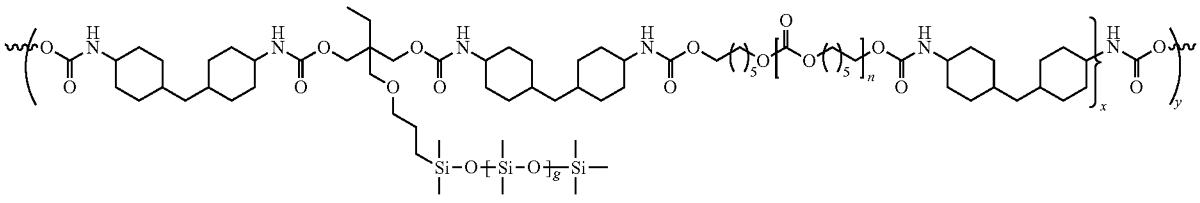

In the Chemical formula 23, x, y and n are as defined in the Chemical formulas 3 to 14, and g is an integer of 5 to 100, respectively.

As one other aspect, the present invention relates to a method for preparing a functionalized thermoplastic polyurethane copolymer comprising the following steps:

(a) reacting a polyol (P) and a diisocyanate (R) to polymerize a pre-polymer; and (b) reacting the pre-polymer polymerized in the (a) with a chain extender comprising a functional group (Fn) to prepare a functionalized thermoplastic polyurethane.

Preferably, the functionalized thermoplastic polyurethane copolymer has the structure of Chemical formula 1 above. Accordingly, the polyol (P) may be one or more kinds of polyols selected from the group consisting of polyether, polycarbonate, polyester and silicone, but not limited thereto. The example of the polyether polyol, polycarbonate polyol, polyester polyol and silicone polyol are as described in the Chemical formula 2. In addition, the average molecular weight of each polyol (P) composing the pre-polymer is 400 g/mol to 10,000 g/mol.

Furthermore, the example of the diisocyanate is also as defined in the Chemical formula 1.

In the (b), the pre-polymer reacts with a chain extender comprising a functional group, and then, it is preferable that the chain extender is represented by the structure of the aforementioned Chemical formula 2. Details of the chain extender are the same as those mentioned in the Chemical formula 2.

In a preferable aspect, in the (a), the equivalence ratio of the polyol (P) and diisocyanate (R) may be 0.5 to 1:1 to 5, as polyol:diisocyanate.

Moreover, in the (b), the equivalence ratio of the pre-polymer and the chain extender comprising a functional group may be 0.5 to 1:1 to 4, as pre-polymer:functional group.

In addition, the polyol (P) may be used by 30% to 97% by weight based on the total weight of the total functionalized thermoplastic polyurethane, and the diisocyanate may be used by 2% to 60% by weight based on the total weight of the total functionalized thermoplastic polyurethane, and the chain extender comprising a functional group may be used by 1% to 20% by weight based on the total weight of the functionalized thermoplastic polyurethane.

As other aspect, the present invention relates to a method for preparation of a functional composite comprising the following steps. Preferably, the functional composite is a medical composite:

i) preparing a functionalized thermoplastic polyurethane; and ii) introducing one or two or more of monomers or polymers selected from the group consisting of an anionic functional group, an amphoteric functional group, a perfluorinated compound, a hydrogel and a silicone polymer.

The i) may be performed specifically, according to the method for preparing the functionalized thermoplastic polyurethane copolymer.

In the ii), one or two or more of monomers or polymers selected from the group consisting of an anionic functional group, an amphoteric functional group, a perfluorinated compound, a hydrogel and a silicone polymer may be introduced using a chemical reaction, for example, thiol-ene reaction, click reaction, hydrogen silylation reaction, thiol-epoxy reaction, and the like. To perform such chemical reaction, the monomer or polymer may comprise a functional group selected from the group consisting of a thiol group, an alkenyl group, an alkynyl group, a silane group, an azide group and an epoxy group. In addition to the functionalized thermoplastic polyurethane and one or two or more of monomers or polymers selected from the group consisting of an anionic functional group, an amphoteric functional group, a perfluorinated compound, a hydrogel and a silicone polymer, substances used for thiol-ene reaction, click reaction, hydrogen silylation or thiol-epoxy reaction, reaction conditions and the like may be appropriately selected from known methods and used.

Preferably, in the ii), when the functionalized thermoplastic polyurethane copolymer is reacted with a compound having an anionic functional group or an amphoteric functional group, a functional composite in which an anionic functional group or an amphoteric functional group is introduced to the side chain or terminal of the thermoplastic polyurethane block copolymer, may be prepared.

Furthermore, in the ii), when the functionalized thermoplastic polyurethane copolymer is reacted with a perfluorinated compound (Poly- and Perfluorinated Compounds: PFCS), a functional composite in which PFC is introduced to the side chain or terminal of the thermoplastic polyurethane block copolymer may be prepared.

In addition, in the ii), when the functionalized thermoplastic polyurethane copolymer is reacted with a compound having hydrogel properties, a functional composite in which a hydrogel functional group is introduced into a side chain or terminal of the thermoplastic polyurethane block copolymer.

Furthermore, in the ii), when the functionalized thermoplastic polyurethane copolymer is reacted with a compound having a silicone functional group, a functional composite in which a silicone group is introduced into a side chain or terminal of the thermoplastic polyurethane block copolymer.

Specifically, the anionic functional group may be selected from the group consisting of anhydrous glutaric anhydride, acetic acid, 2,7-oxepanedione, dihydro-furan-2,5-dione, oxepane-2,7-dione, succinic anhydride, maleic anhydride, citraconic anhydride, diethylenetriamine pentaacetic anhydride, iodoacetate, chloroacetic acid, 1,3-propane sultone, 1,4-butane sultone, 1-propene-1,3-sultone, 1,8-naphthalene sultone and combinations thereof, but not limited thereto.

The amphoteric functional group may be selected from the group consisting of phosphorylcholine, phosphoryl ethanolamine, phosphoryl-serine, sulfobetaine, carboxybetaine, and combinations thereof, but not limited thereto.

The perfluorinated compound may be a compound represented by the chemical formula of $CF_3$—$(CF_2)_e$—$(CH_2)_t$-A, and then, e may be 3~25, and t may be 0~10, and A may be selected from the group consisting of SH, azide, allyl, propargyl groups and combinations thereof, but not limited thereto.

The hydrogel may be selected from the group consisting of Pluronic F-127, polyethylene oxide-polypropylene oxide-polyethylene oxide (PEO-PPO-PEO), polystyrene-co-maleic anhydride, polyethylene glycol-poly L-lactic acid-polyethylene glycol (PEG-PLLA-PEG), poly N-isopropyl acrylamide (PNIPAAm) or a copolymer of polyethylene oxide and polypropylene oxide and combinations thereof, but not limited thereto.

The silicone may be selected from the group consisting of polydimethylsiloxane (PDMS), polyarylsiloxane and polyalkylsiloxane and combinations thereof, but not limited thereto.

Because the functionalized thermoplastic polyurethane according to the present invention prepared by the above method comprises a chain extender comprising a functional group, it is possible to introduce various functionalities according to the user's need by a relatively easy chemical method, so that the long-term functionality may be maintained, different from the conventional method (one-time use) in which the functionality is introduced by a physical method (for example, coating or dispersion).

Specifically, the functionalized thermoplastic polyurethane according to the present invention may have an advantage of introducing additional functionality as needed, while maintaining the same performance as a general thermoplastic polyurethane (for example, water absorption rate, hydrophobicity or hydrophilicity, excellent mechanical properties). Although not limited thereto, it is designed to prepare various functionalities by a relatively easy chemical method according to the user's convenience, for example, such as preparing a thermoplastic polyurethane which can increase chemical resistance and hydrophobicity by introducing a perfluorinated compound into a thermoplastic polyurethane having excellent mechanical properties, or can improve hydrophilic properties by introducing an amphoteric ion into a thermoplastic polyurethane having hydrophobic properties and inhibit protein adsorption, Furthermore, the method for introducing a functional group into a polyol or diisocyanate is difficult to commercialize due to difficulties in reproducibility, productivity and purification, and the like, whereas the introduction of a functional group in a chain extender is advantageous for mass production because synthesis and purification are relatively easy.

In other aspect, the present invention provides an article comprising the functionalized thermoplastic polyurethane copolymer and/or a functional composite comprising the functionalized thermoplastic polyurethane copolymer. Such article may be prepared by a method by calendering, casting, coating, compounding, extrusion, foaming, laminating, blow molding, compression molding, injection molding, thermoforming, transfer molding, cast molding, rotational molding, spun or melt bonding, or combinations thereof for the thermoplastic polyurethane copolymer and/or functional composite according to the present invention.

The article of the present invention may further comprise one or more coloring agents, anti-oxidants (including phenol resins, phosphite, thioester and/or amine), antiozonants, stabilizing agents, lubricants, inhibiting agents, hydrolysis stabilizers, light stabilizers, benzotriazole UV absorbents, heat stabilizers, stabilizers to prevent discoloration, dyes, pigments, reinforcing agents or any combination thereof, together with the thermoplastic polyurethane copolymer and/or functional composite.

Preferably, the article according to the present invention is a medical device or part thereof, and for example, it may or may not be implantable in the body of a human or an animal, and for example, it may be one or more kinds selected from the group consisting of an electrochemical biosensor, a pacemaker lead, an artificial organ, an artificial heart, a heart valve, an artificial tendon, an artery or vein, an implant, a medical bag, a medical valve, a medical tube, a drug delivery device, a bioabsorbable implant, a medical prototype, a medical model, an orthodontic appliance, a bone, a dental appliance and a surgical tool, or a part thereof. More preferably, the article according to the present invention may be a protective film used in an electrochemical biosensor such as a continuous blood glucose monitoring sensor.

MODE FOR INVENTION

Hereinafter, the present invention will be described in more detail by the following examples. However, the following examples are for illustrative purposes only and the contents of the present invention are not limited by the following examples.

Example 1: Preparation of Functionalized Thermoplastic Polyurethane According to the Present Invention

(1) Synthesis of Chain Extender

1-1) Synthesis of (5-ethyl-2,2-dimethyl-1,3dioxan-5-yl)methanol

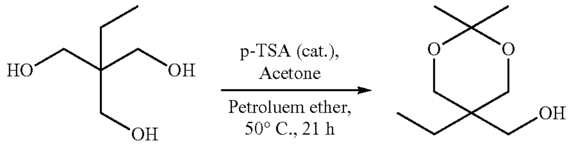

100 g (0.75 mol) of trimethylolpropane and 200 mL acetone were added to a 1 L two-necked round-bottom flask, and dissolved in 200 mL of petroleum ether. To this mixture, p-toluenesulfonic acid (0.13 g, 0.75 mmol) was added and heated to 50° C. and stirred for 21 hours. After completion of the reaction, it was cooled to room temperature, and the reaction solvent was removed by concentration under reduced pressure. The reaction mixture remaining in the flask was purified by vacuum distillation (0.1 torr, 90° C.) to obtain a clear colorless liquid. (93.0 g, 72%)

1-2) Synthesis of 5-((allyloxy)methyl)-5-ethyl-2,2 dimethyl-1,3-dioxane

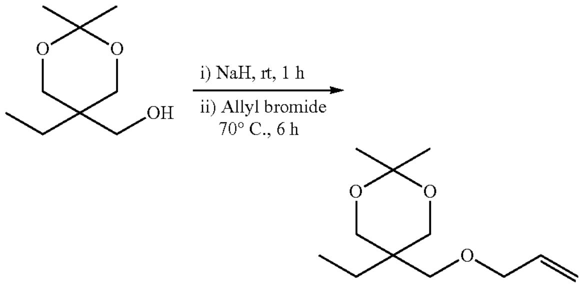

10.0 g (57.4 mmol) of (5-ethyl-2,2-dimethyl-1,3dioxan-5-yl)methanol was dissolved in anhydrous tetrahydrofuran (100 mL) under argon in a 250 mL two-necked round-bottom flask, and then sodium hydride 2.8 g (68.9 mmol) was added. This mixture was stirred at a room temperature for one hour, and then allylbromide 8.3 g (68.9 mmol) was added and heated to 70° C. under argon and stirred for 6 hours. After completion of the reaction, the reaction mixture was cooled to room temperature and the solvent, tetrahydrofuran was removed by concentration under reduced pressure, and then extracted with water (30 mL) and ethylacetate (60 mL×3). The extracted organic layer was collected and dried with magnesium sulfate and concentrated under reduced pressure to remove the solvent. The yellow liquid, 5-ethyl-5-(((2-hexyldecyl)methyl)-2,2-dimethyl-1,3-dioxane was obtained. (11.7 g, 95%)

1-3) Synthesis of 2-((allyloxy)methyl)-2-ethylpropane-1,3-diol

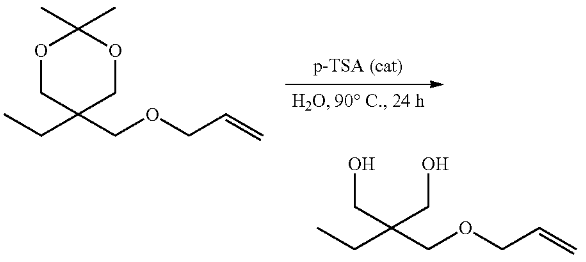

(hexane:ethylacetate=2:1) Finally, a transparent liquid 2-((allyloxy)methyl)-2-ethylpropane-1,3-diol(CE-allyl) was obtained (8.6 g, 88%).

(2) Preparation of Pre-Polymer Composed of Polyol and Diisocyanate and Synthesis of Polyurethane Copolymer Using Functionalized Chain Extender By reacting the chain extender prepared in Example 1 by the method as below, the functionalized thermoplastic polyurethane copolymer according to the present invention was prepared.

2-1) Synthesis of Polyether Functionalized Thermoplastic Polyurethane

2-1-1) Synthesis of PEG-PU-CE-Allyl

According to Reaction formula 1 below, PEG-PU-CE-allyl was synthesized.

[Reaction formula 1]

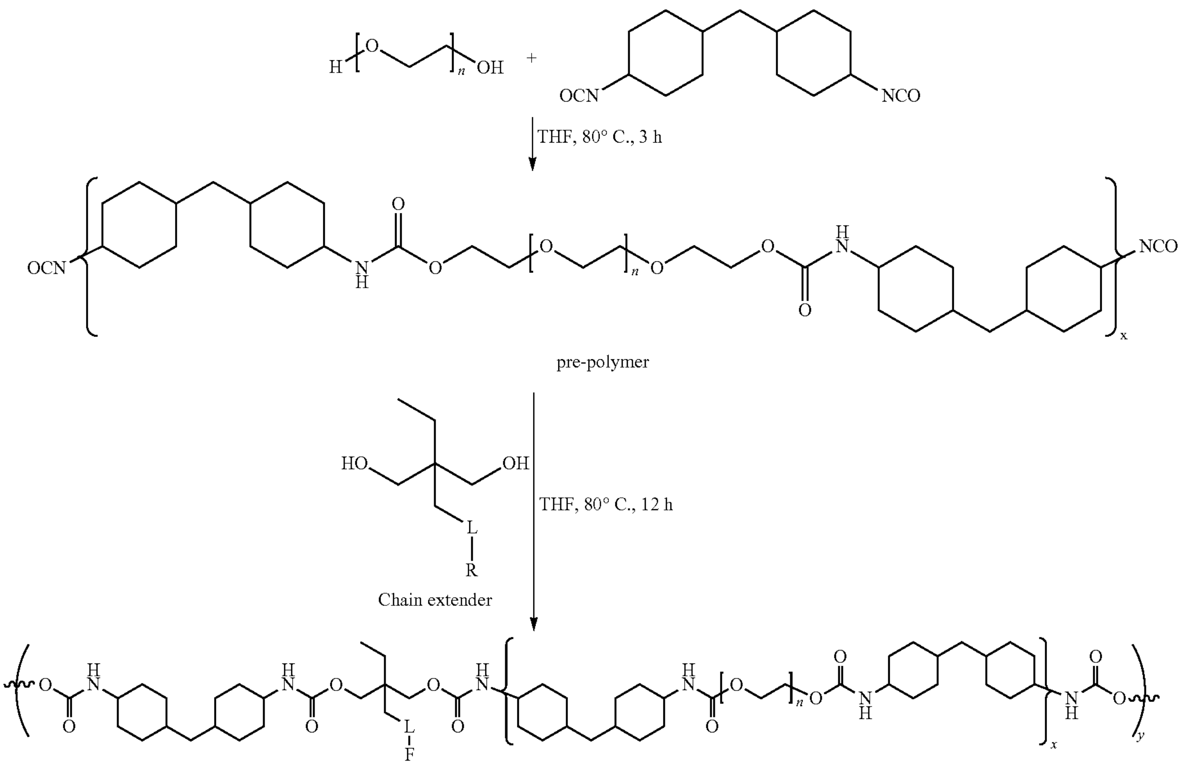

13.0 g (60 mmol) of 5-((allyloxy)methyl)5-ethyl-2,2dimethyl-1,3-dioxane and a catalytic amount of p-toluenesulfonic acid were added in a 500 mL two-necked round-bottom flask, and mixed with distilled water 200 ml and stirred at 90° C. for 24 hours. After completion of the reaction, the reaction mixture was cooled to room temperature and extracted with ethylacetate (100 mL×3). The organic layer was cooled and dried with magnesium sulfate and concentrated under reduced pressure to remove the solvent. The non-purified reactant was purified by column chromatography using ethyl acetate and hexane as a developing solvent.

Before reaction, polyethylene glycol was dried in a vacuum oven at 70° C. for 24 hours and used. Other liquid reagents were used after removing moisture using a 4 Å Molecular sieve. An overhead stirrer, a cooler, a gas inlet pipe and a rubber septum were installed in a 1 L double-jacket reactor, and polyethylene glycol ($M_n$=1,000 g/mol) 10.0 g (10 mmol) and 20 mL of anhydrous tetrahydrofuran were added to conduct argon degassing for 15 minutes. Dibutyltin dilaurate 0.6 g and cyclohexylmethylene diisocyanate 5.2 g (20 mmol) which were catalysts were added to the reactor using a gas tight syringe in order and heated at 80° C. for 3 hours. After the reaction, the NCO (%) content of the synthesized polyurethane pre-polymer was confirmed using a back titration method. An overhead stirrer, a cooler, a gas inlet pipe and a rubber septum were installed in a 1 L double-jacket reactor, and the prepared pre-polymer was added, and then the synthesized chain extender CE-allyl (10 mmol) was slowly added using a syringe pump and heated at 80° C. for 12 hours. The polyurethane with high viscosity synthesized after completion of the reaction was dissolved in THF and precipitated by slowly dropping in a beaker having diethylether. The precipitated white solid was added in a vacuum oven and dried at a room temperature for 24 hours. Finally, the white solid thermoplastic polyurethane copolymer PEG-PU-CE-allyl as below was prepared. (15 g)

[Chemical formula 3]

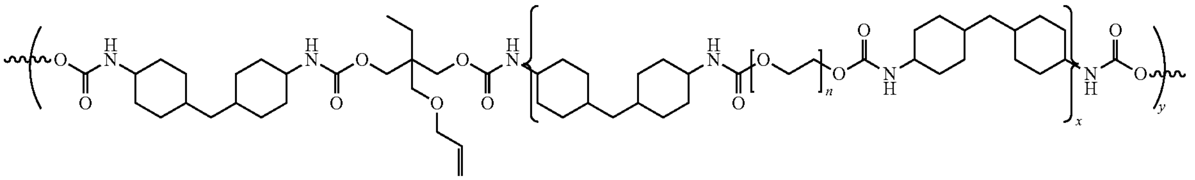

2-2) Synthesis of Polycarbonate Functionalized Thermoplastic Polyurethane

2-2-1) Synthesis of PC-PU-CE-Allyl

According to Reaction formula 2 below, PC-PU-CE-allyl was synthesized.

[Reaction formula 2]

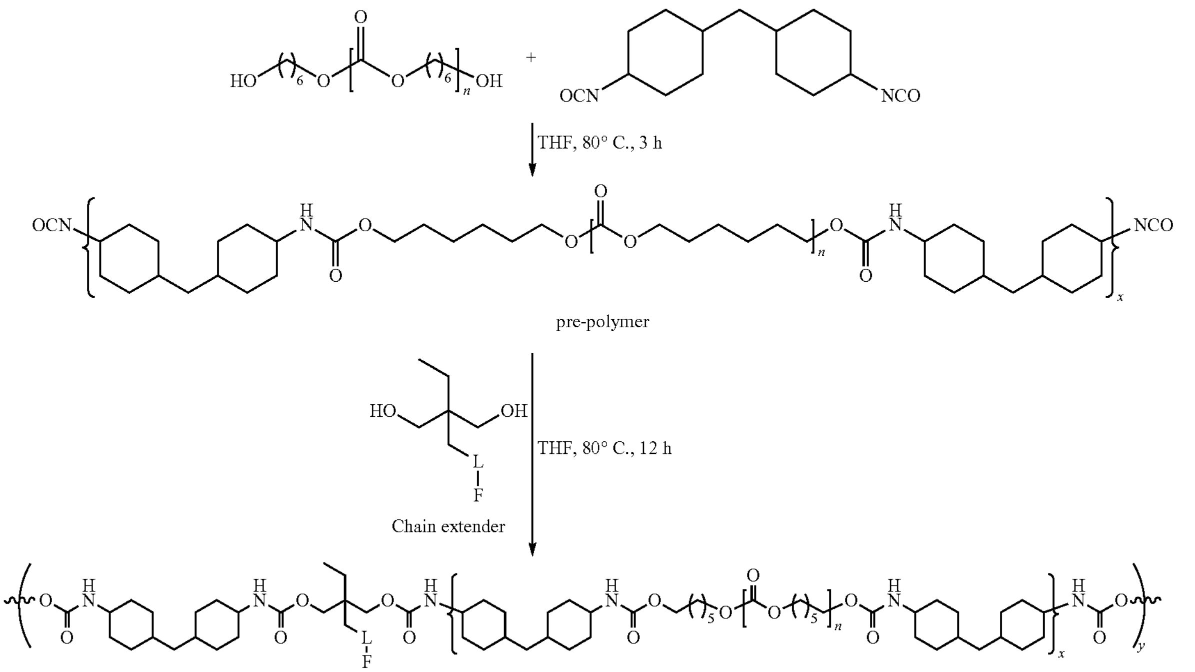

Before reaction, polyhexamethylene carbonate was dried in a vacuum oven at 70° C. for 24 hours and used. Other liquid reagents were used after removing moisture using a 4 Å Molecular sieve. An overhead stirrer, a cooler, a gas inlet pipe and a rubber septum were installed in a 1 L double-jacket reactor, and polyhexamethylene carbonate ($M_n$=2,000 g/mol) 20.0 g (10 mmol) and 40 mL of anhydrous tetrahydrofuran were added to conduct argon degassing for 15 minutes. Dibutyltin dilaurate 0.6 g and cyclohexylmethylene diisocyanate 5.2 g (20 mmol) which were catalysts were added to the reactor using a gas tight syringe in order and heated at 80° C. for 3 hours. After the reaction, the NCO (%) content of the synthesized polyurethane pre-polymer was confirmed using a back titration method. An overhead stirrer, a cooler, a gas inlet pipe and a rubber septum were installed in a 1 L double-jacket reactor, and the prepared pre-polymer was added, and then the synthesized chain extender CE-allyl (10 mmol) was slowly added using a syringe pump and heated at 80° C. for 12 hours. The polyurethane with high viscosity synthesized after completion of the reaction was dissolved in THF and precipitated by slowly dropping in a beaker having diethylether. The precipitated white solid was added in a vacuum oven and dried at a room temperature for 24 hours. Finally, the white solid thermoplastic polyurethane copolymer PC-PU-CE-allyl as below was prepared. (20.0 g)

[Chemical formula 7]

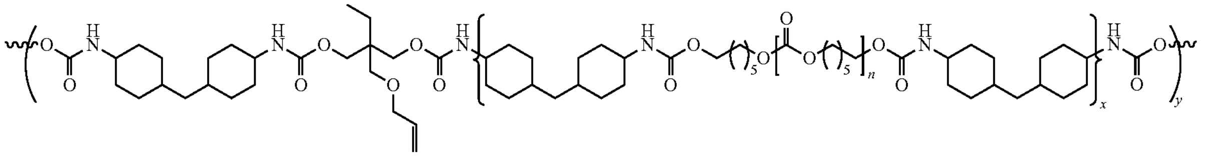

2-3) Synthesis of Polydimethylsiloxane Functionalized Thermoplastic Polyurethane

2-3-1) Synthesis of PDMS-PU-CE-Allyl

According to Reaction formula 3 below, PDMS-PU-CE-allyl was synthesized.

cyanate 5.2 g (20 mmol) which were catalysts were added to the reactor using a gas tight syringe in order and heated at 80° C. for 3 hours. After the reaction, the NCO (%) content of the synthesized polyurethane pre-polymer was confirmed using a back titration method. An overhead stirrer, a cooler, a gas inlet pipe and a rubber septum were installed in a 1 L double-jacket reactor, and the prepared pre-polymer was

[Reaction formula 3]

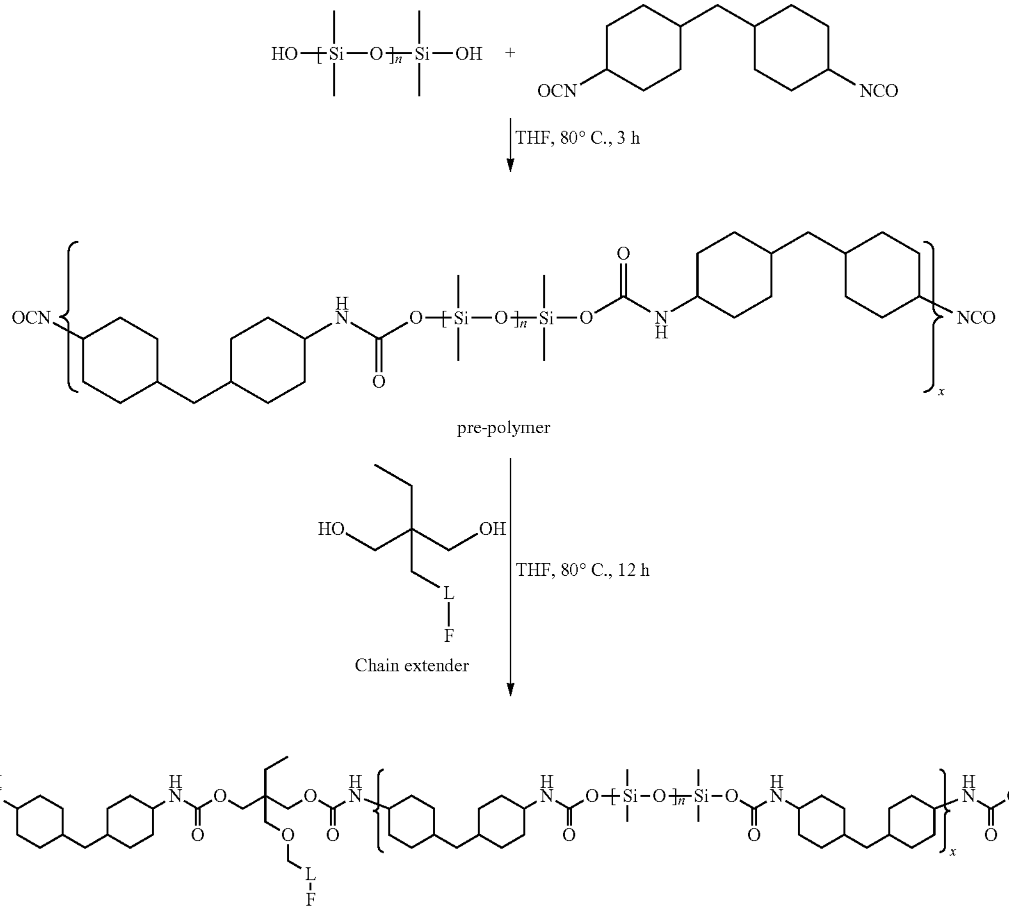

Before reaction, polydimethyl siloxane was dried in a vacuum oven at 70° C. for 24 hours and used. Other liquid reagents were used after removing moisture using a 4 Å Molecular sieve. An overhead stirrer, a cooler, a gas inlet pipe and a rubber septum were installed in a 1 L double-jacket reactor, and polydimethyl siloxane ($M_n$=900 g/mol) 9.0 g (10 mmol) and 10 mL of anhydrous tetrahydrofuran were added to conduct argon degassing for 15 minutes. Dibutyltin dilaurate 0.6 g and cyclohexylmethylene diisoadded, and then the synthesized chain extender CE-allyl (10 mmol) was slowly added using a syringe pump and heated at 80° C. for 12 hours. The polyurethane with high viscosity synthesized after completion of the reaction was dissolved in THF and precipitated by slowly dropping in a beaker having diethylether. The precipitated white solid was added in a vacuum oven and dried at a room temperature for 24 hours. Finally, the white solid thermoplastic polyurethane copolymer PDMS-PU-CE-allyl as below was prepared. (11.0 g)

[Chemical formula 11]

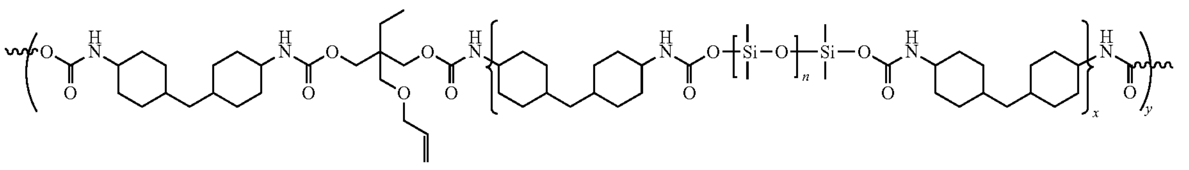

Example 2: Preparation of Functional Thermoplastic Polyurethane in which a Monomer and a Polymer Having Various Functional Groups into the Functionalized Thermoplastic Polyurethane According to the Present Invention

(1) Synthesis of Amphoteric Ion-Introduced Functional Thermoplastic Polyurethane

[Chemical formula 19]

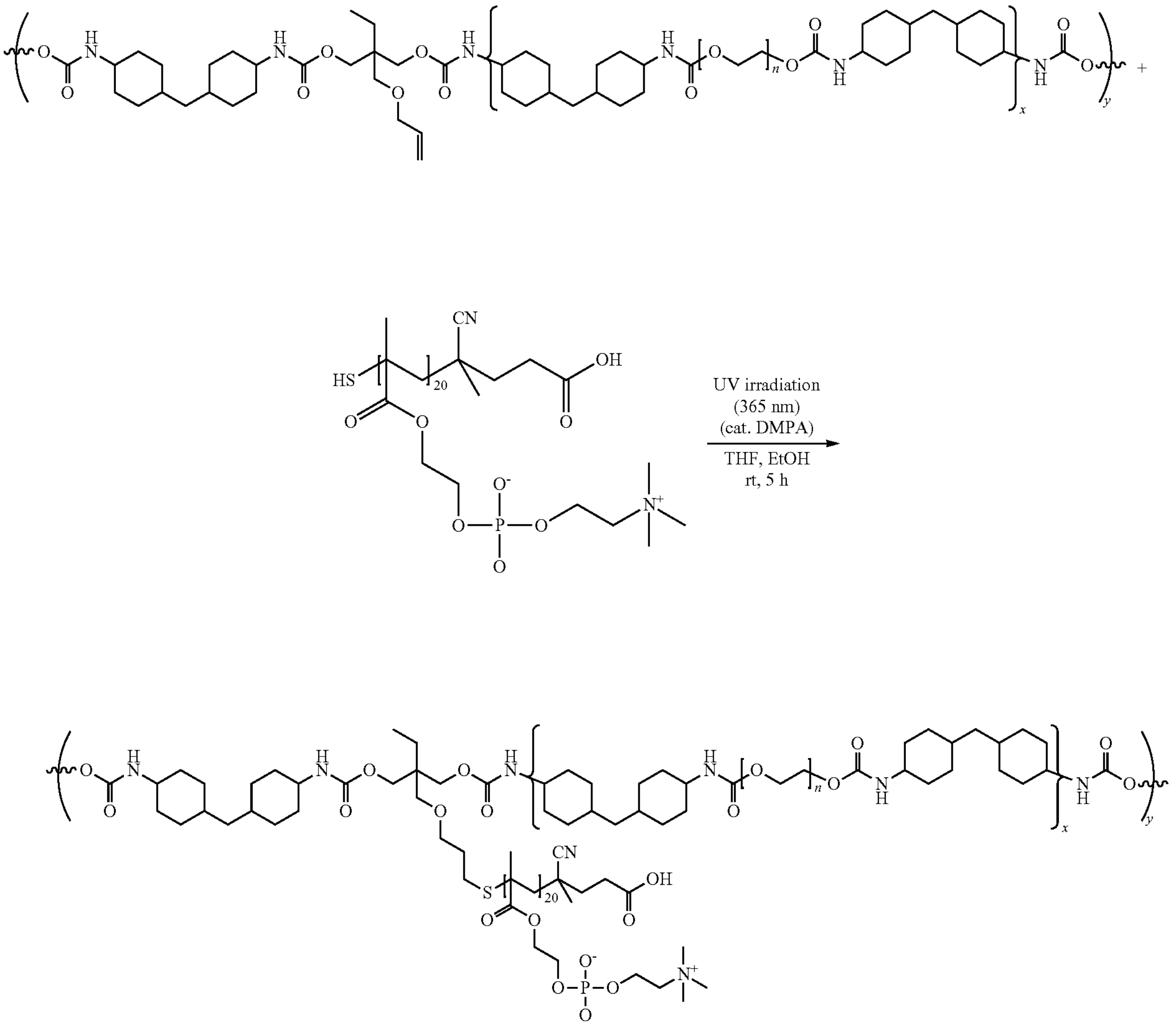

PEG-PU-CE-allyl 3.0 g (0.2 mmol/allyl group), terminal monothiol (methylacryloloxyethyl phosphoryl choline) polymer (molecular weight: ~6,000 g/mol) 1.2 g (~0.2 mmol) and DMPA (13 mg, 0.05 mmol) were dissolved in 25 mL ethanol with 50 mL tetrahydrofuran in a 250 mL round-bottom flask under argon atmosphere, and then argon degassing was conducted for 15 minutes. This reaction mixture was added in a UV reactor and light of 315~400 nm was irradiated for 5 hours. After completion of the reaction, the synthesized polyurethane was precipitated by slowly dropping in a beaker having diethylether. The precipitated white solid was added in a vacuum oven and dried at a room temperature for 24 hours. Finally, the white solid functional thermoplastic polyurethane copolymer as [Chemical formula 19] was prepared (3.7 g, 88%).

(2) Synthesis of Hydrogel Polymer-Introduced Functional Thermoplastic Polyurethane

[Chemical formula 20]

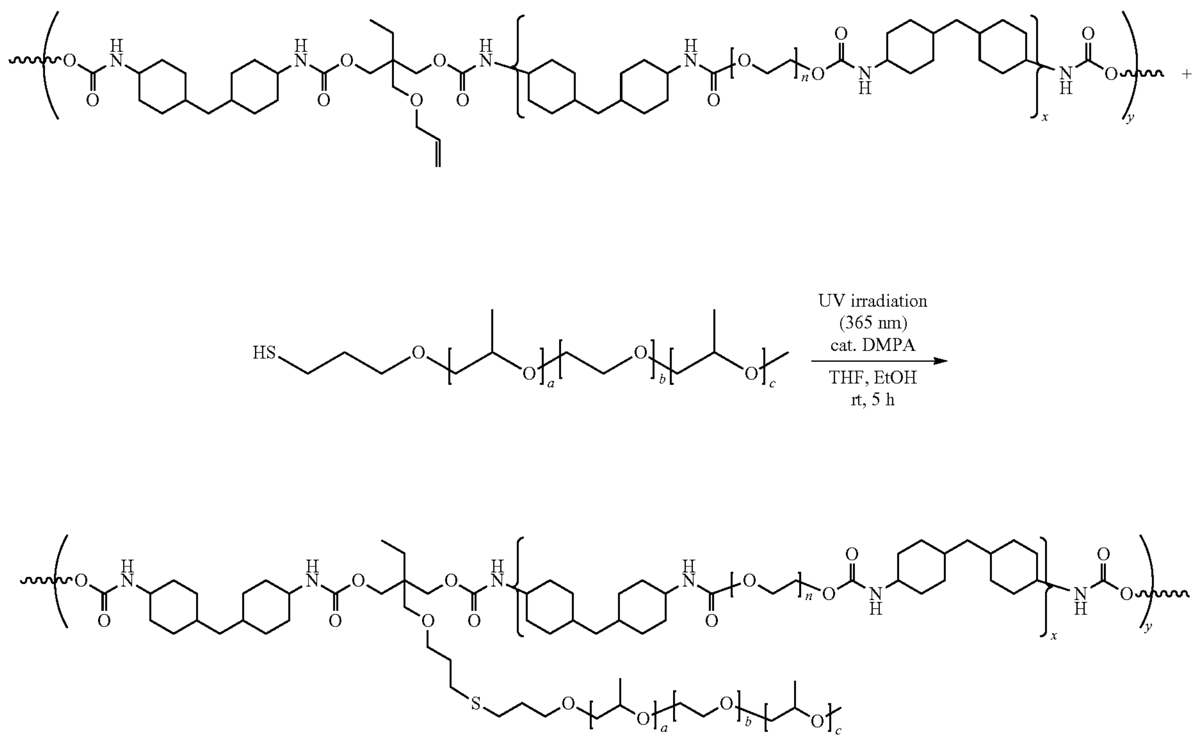

PEG-PU-CE-allyl 3.0 g (0.2 mmol/allyl group), terminal monothiol poly(propylene glycol-ethylene glycol-propylene glycol) (molecular weight: ~2,000 g/mol) 0.4 g (0.2 mmol) and DMPA (14 mg, 0.05 mmol) were dissolved in 25 mL ethanol with 50 mL tetrahydrofuran in a 250 mL round-bottom flask under argon atmosphere, and then argon degassing was conducted for 15 minutes. This reaction mixture was added in a UV reactor and light of 315~400 nm was irradiated for 5 hours. After completion of the reaction, the synthesized polyurethane was precipitated by slowly dropping in a beaker having diethylether. The precipitated white solid was added in a vacuum oven and dried at a room temperature for 24 hours. Finally, the white solid functional thermoplastic polyurethane copolymer as [Chemical formula 20] was prepared (3.2 g, 94%).

[Chemical formula 21]

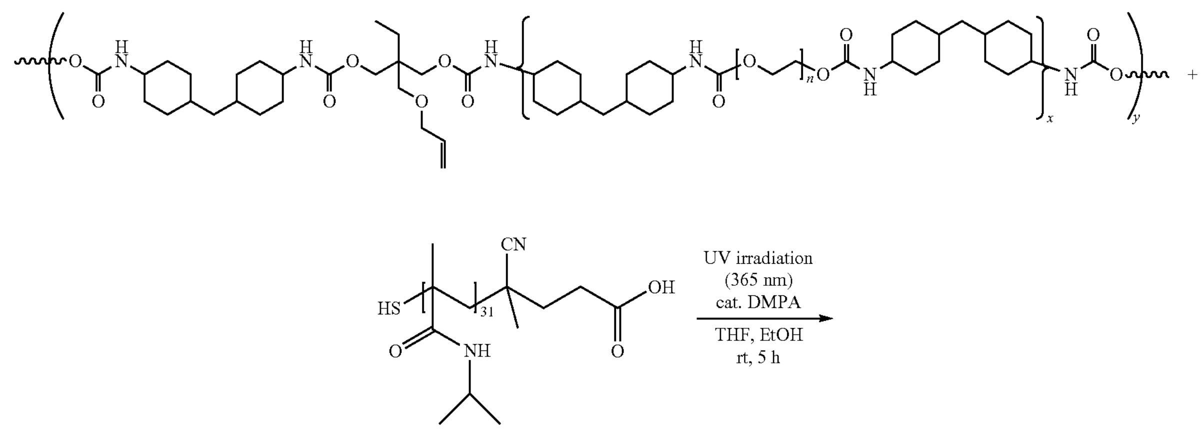

-continued

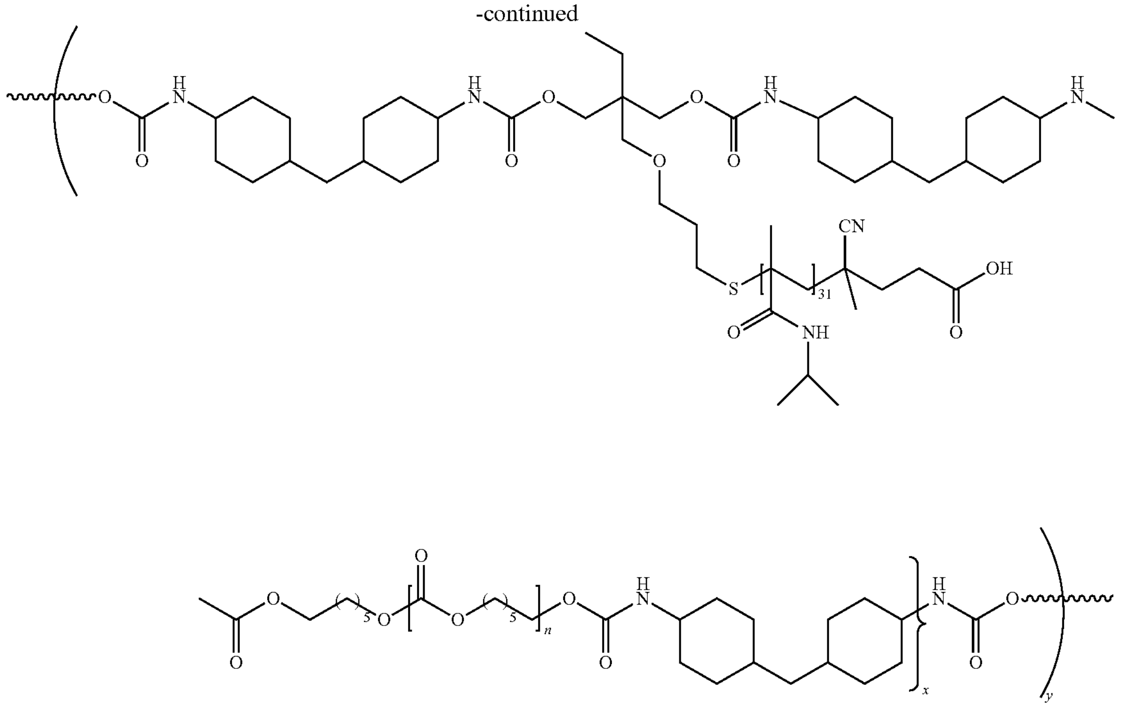

PEG-PU-CE-allyl 3.0 g (0.2 mmol/allyl group), terminal monothiol poly(N-isopropylacrylamide) (molecular weight: ~4,000 g/mol) 0.8 g (0.2 mmol) and DMPA (14 mg, 0.05 mmol) were dissolved in 25 mL ethanol with 50 mL tetrahydrofuran in a 250 mL round-bottom flask under argon atmosphere, and then argon degassing was conducted for 15 minutes. This reaction mixture was added in a UV reactor and light of 315~400 nm was irradiated for 5 hours. After completion of the reaction, the synthesized polyurethane was precipitated by slowly dropping in a beaker having diethylether. The precipitated white solid was added in a vacuum oven and dried at a room temperature for 24 hours. Finally, the white solid functional thermoplastic polyurethane copolymer as [Chemical formula 21] was prepared (3.5 g, 92%).

(3) Synthesis of Perfluorinated Compound-Introduced Functional Thermoplastic Polyurethane

[Chemical formula 22]

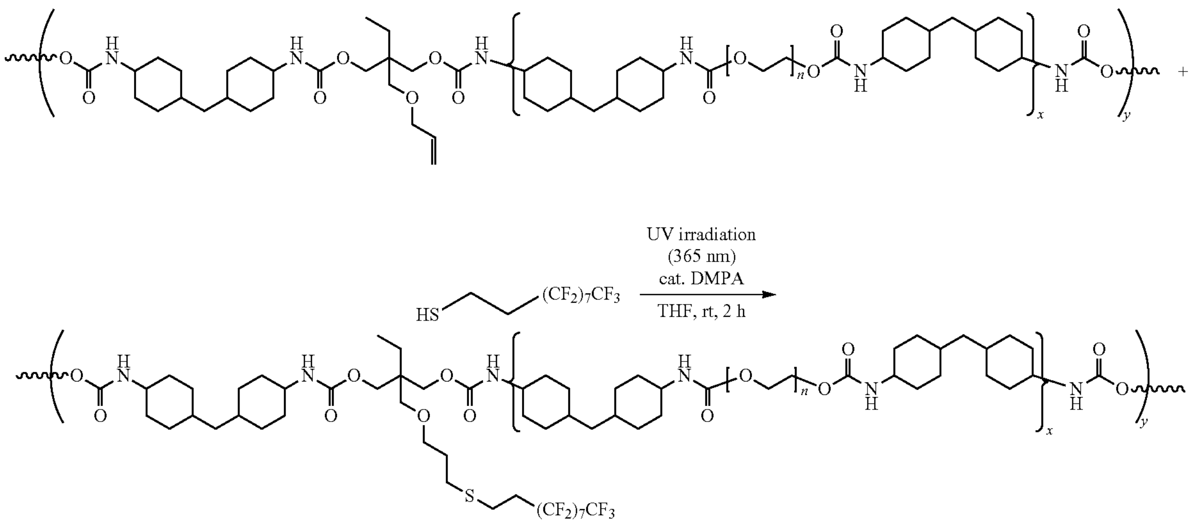

PEG-PU-CE-allyl 6.0 g (0.4 mmol/allyl group), 1H,1H, 2H,2H-perfluorodecanethiol 0.24 g (0.5 mmol) and DMPA (28 mg, 0.1 mmol) were dissolved in 25 mL ethanol with 100 mL tetrahydrofuran in a 250 mL round-bottom flask under argon atmosphere, and then argon degassing was conducted for 15 minutes. This reaction mixture was added in a UV reactor and light of 315~400 nm was irradiated for 2 hours. After completion of the reaction, the synthesized polyurethane was precipitated by slowly dropping in a beaker having diethylether. The precipitated white solid was added in a vacuum oven and dried at a room temperature for 24 hours. Finally, the white solid functional thermoplastic polyurethane copolymer as [Chemical formula 22] was prepared (5.5 g, 88%).

(4) Synthesis of Silicone Polymer-Introduced Functional Thermoplastic Polyurethane

[Chemical formula 23]

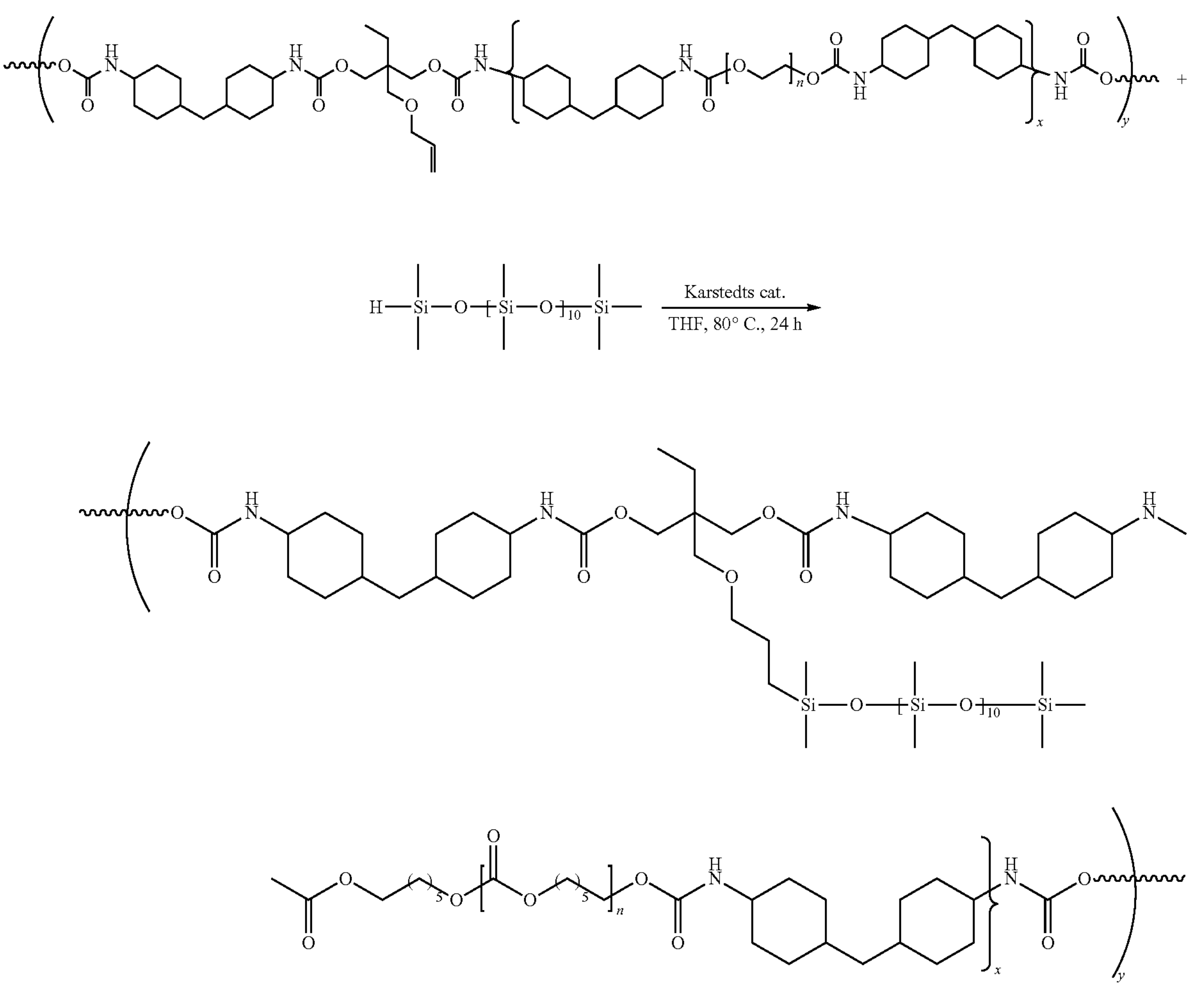

PEG-PU-CE-allyl 3.0 g (0.2 mmol/allyl group), monohydropoly(dimethylsiloxane) (molecular weight: 800 g/mol) 0.24 g (0.3 mmol) was dissolved in 25 mL tetrahydrofuran in a 100 mL round-bottom flask, and then argon degassing was conducted for 15 minutes. To this reaction mixture, platinum(0)-1,3-divinyl-1,1,3,3,-tetramethyldisiloxane complex solution 10 μL was added and then heated at 80° C. and stirred for 24 hours. After completion of the reaction, the reaction mixture was cooled to room temperature and an excess tetrahydrofuran (200 mL) was added and sufficiently diluted and then filtered in Celite/Charcoal to remove a platinum catalyst. Using a vacuum concentrator, the solvent was removed, leaving only 100 mL. The reaction mixture remaining in the flask was precipitated by slowly dropping in a beaker having diethylether. The precipitated white solid was added in a vacuum oven and dried at a room temperature for 24 hours. Finally, the white solid functional thermoplastic polyurethane copolymer as [Chemical formula 23] was prepared (2.5 g, 77%).

The invention claimed is:

1. A method for preparation of a functionalized thermoplastic polyurethane, comprising (a) reacting a polyol (P) and a diisocyanate (R) to polymerize a pre-polymer; and (b) reacting the pre-polymer polymerized in the (a) with a chain extender comprising a functional group (Fn) to prepare a functionalized thermoplastic polyurethane, wherein the functionalized thermoplastic polyurethane copolymer is represented by Chemical formula 1 below:

[Chemical formula 1]

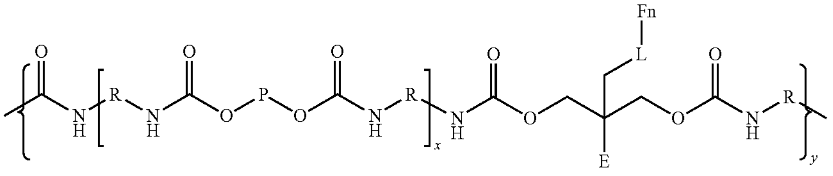

in the Chemical formula 1,

Fn is selected from the group consisting of

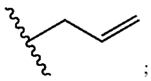
;
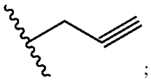
;
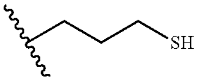
or
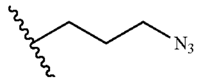

L is —O—; and

E is ethyl; and

P is a polyol; and

R is a diisocyanate; and x is an integer of 2 to 50; and y is an integer of 2 to 100;

the polyol is one or more kinds selected from the group consisting of polyethyleneglycol (PEG), polypropyleneglycol (PPG), polytetramethyleneglycol (PTMG), poly (1,6-hexamethylene carbonate)diol (PHMCD), polydimethyl siloxane (PDMS), and combinations thereof;

the mean molecular weight of each polyol (P) is 400 g/mol to 10,000 g/mol;

the diisocyanate (R) is one or more kinds selected from the group consisting of 4,4'-dicyclohexylmethane diisocyanate (HMDI), 4,4'-diphenylmethane diisocyanate (MDI), and hexamethylene diisocyanate;

wherein a chain extender of Chemical formula 2 below is introduced:

[Chemical formula 2]

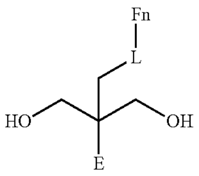

the chain extender is selected from the group consisting of Chemical formulas 15 to 18 below:

[Chemical formula 15]

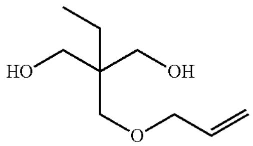

[Chemical formula 16]

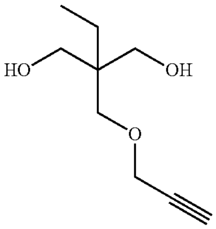

[Chemical formula 17]

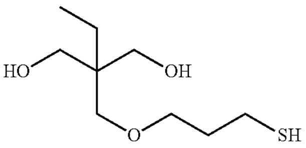

[Chemical formula 18]

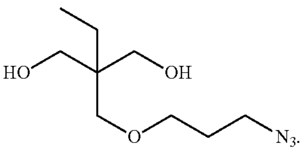

2. The method for preparation of the functionalized thermoplastic polyurethane according to claim 1, wherein the diisocyanate is used as 2% to 60% by weight based on the total weight of the total functionalized thermoplastic polyurethane; and the chain extender comprising a functional group is used as 1% to 20% by weight based on the total weight of the total functionalized thermoplastic polyurethane.

* * * * *